(12) United States Patent
Lee

(10) Patent No.: US 12,264,204 B2
(45) Date of Patent: Apr. 1, 2025

(54) PEPTIDE FOR IMPROVING MEMORY AND PREVENTING OR ALLEVIATING COGNITIVE DYSFUNCTION, COMPOSITION COMPRISING THE SAME, AND METHOD FOR PRODUCING THE SAME

(71) Applicant: NATURESENSE CO., LTD., Uiwang-Si (KR)

(72) Inventor: Ji Won Lee, Gwacheon-si (KR)

(73) Assignee: NATURESENSE CO., LTD., Uiwang-Si (KR)

( * ) Notice: Subject to any disclaimer, the term of this patent is extended or adjusted under 35 U.S.C. 154(b) by 0 days.

(21) Appl. No.: 17/023,248

(22) Filed: Sep. 16, 2020

(65) Prior Publication Data
US 2021/0115086 A1    Apr. 22, 2021

(30) Foreign Application Priority Data

| Oct. 16, 2019 | (KR) | 10-2019-0128320 |
| Oct. 22, 2019 | (KR) | 10-2019-0131513 |
| Oct. 25, 2019 | (KR) | 10-2019-0133333 |
| Oct. 28, 2019 | (KR) | 10-2019-0134292 |
| Oct. 28, 2019 | (KR) | 10-2019-0134293 |
| Nov. 7, 2019 | (KR) | 10-2019-0141469 |
| Nov. 12, 2019 | (KR) | 10-2019-0144273 |
| Nov. 12, 2019 | (KR) | 10-2019-0144275 |
| Nov. 12, 2019 | (KR) | 10-2019-0144448 |
| Nov. 12, 2019 | (KR) | 10-2019-0144499 |
| Nov. 21, 2019 | (KR) | 10-2019-0150276 |
| Nov. 26, 2019 | (KR) | 10-2019-0153393 |
| Dec. 5, 2019 | (KR) | 10-2019-0160472 |
| Dec. 5, 2019 | (KR) | 10-2019-0160478 |
| Dec. 5, 2019 | (KR) | 10-2019-0160480 |
| Dec. 5, 2019 | (KR) | 10-2019-0160484 |
| Dec. 9, 2019 | (KR) | 10-2019-0162437 |
| Dec. 9, 2019 | (KR) | 10-2019-0162438 |
| Dec. 9, 2019 | (KR) | 10-2019-0162439 |
| Dec. 9, 2019 | (KR) | 10-2019-0162441 |

(51) Int. Cl.
C07K 5/10       (2006.01)
C07K 1/12       (2006.01)
C12P 21/06      (2006.01)

(52) U.S. Cl.
CPC .................. C07K 5/10 (2013.01); C07K 1/12 (2013.01); C12P 21/06 (2013.01)

(58) Field of Classification Search
CPC .......... C07K 5/10; C07K 1/12; C07K 5/1008; C07K 5/101; C07K 14/43586; C07K 5/1016; C12P 21/06; A61P 25/28; C12N 9/50
See application file for complete search history.

(56) References Cited

U.S. PATENT DOCUMENTS

| 10,010,574 B2 | 7/2018 | Kim et al. | |
| 2007/0260039 A1 | 11/2007 | Karatzas et al. | |
| 2008/0280834 A1* | 11/2008 | Zarnegar | A61P 35/00 514/18.9 |
| 2010/0189649 A1* | 7/2010 | Greene | A61P 35/00 424/9.1 |
| 2011/0129531 A1 | 6/2011 | Collette et al. | |

FOREIGN PATENT DOCUMENTS

| CN | 109879988 A | 6/2019 | |
| JP | 2003002898 A | 1/2003 | |
| JP | 2008289370 A | 12/2008 | |
| JP | 2015101571 A | 6/2015 | |
| KR | 20040073425 A | 8/2004 | |
| KR | 20050040124 A | 5/2005 | |
| KR | 100494358 B1 | 6/2005 | |
| KR | 100575229 B1 | 4/2006 | |
| KR | 101430387 B1 | 8/2014 | |
| KR | 101434682 B1 | 8/2014 | |
| KR | 101706296 B1 | 2/2017 | |
| KR | 101931363 B1 | 12/2018 | |
| WO | WO0191700 A2 | 12/2001 | |
| WO | WO2006014033 A1 | 2/2006 | |
| WO | WO-2007064997 A2 * | 6/2007 | ................ A61P 1/16 |
| WO | WO2012008494 A1 | 1/2012 | |
| WO | WO2014039074 A2 | 3/2014 | |
| WO | WO2014152097 A1 | 9/2014 | |
| WO | WO2015194564 A1 | 12/2015 | |
| WO | WO2017079832 A1 | 5/2017 | |
| WO | WO2019094700 A1 | 5/2019 | |

OTHER PUBLICATIONS

Sutherland et al, Mol. Biol. Evol, 2007, 24 (11), 2424-2432 (Year: 2007).*
Saito et al Biosci. Biotech. Biochem., 1994, 58 (10), 1767-1771). (Year: 1994).*
Flynn et al (STN abstract from US20050288286A1, Dec. 29, 2005) (Year: 2005).*
Betts et al [Bioinformatics for Geneticists. Edited by M.R.Barnes and I.C.Gray, 2003, John Wiley & Sons, Ltd]. (Year: 2003).*
You et al, Food Research International, 2010, 43(3), 848-855. (Year: 2010).*

(Continued)

*Primary Examiner* — Sudhakar Katakam
(74) *Attorney, Agent, or Firm* — STIP Law Group, LLC

(57) ABSTRACT

The present disclosure relates to a method for producing a silk-derived peptide. The method for producing a silk-derived peptide may comprise steps of: dissolving silk fibroin; hydrolyzing the dissolved silk fibroin by treatment with an enzyme mixture comprising a first protease, which comprises bromelain, and a second protease comprising any one selected from the group consisting of Flavourzyme, Protamex, neutrase, Veron W, Sumizyme, zingibn, calpain, protease NP, validase, and mixtures thereof; and removing the proteases.

3 Claims, 8 Drawing Sheets

(56) References Cited

OTHER PUBLICATIONS

Fibroin heavy chain precursor [Bombyx mori], NCBI GenBank Accession No. NP_001106733.1, Sep. 21, 2019, retrieved from https://www.ncbi.nlm.nih.gov/protein/164448672?sat=4&satkey=343311997.

Bisaccia F et al, Migration of monocytes in the presence of elastolytic fragments of elastin and in synthetic derivates. Structure-activity relationship, Oct. 1994, vol. 44, No. 4, pp. 332-341, Int J Pept Protein Res, Hoboken, USA, abstract only.

Riko Matsui et al, Designing antioxidant peptides based on the antioxidant properties of the amino acid side-chains, Food Chemistry, 2018, vol. 245, pp. 750-755, Elsevier, Amsterdam, Netherlands.

Chen Ning et al, Preparation and Antioxidant Activities of Walnut Protein Hydrolysates, Chemical Journal of Chinese Universities, 2013, vol. 34, No. 1 pp. 72-76, Chem. J. Chinese Universities, Changchun City, China, English translation of abstract.

V.Guantieri et al, Synthetic Fragments and Analogues of Elastin. 1. The Synthesis, Biopolymers, 1990, vol. 29, pp. 845-854, John Wiley & Sons, Inc, Hoboken, USA.

Ji an Joung et al, Application of Food-Grade Proteolytic Enzyme for the Hydrolysis of Regenerated Silk Fibroin from Bombyx mori, Hindawi Journal of Chemistry, 2018, vol. 2018, Article ID 1285823, pp. 1-10, Hindawi, London, United Kingdom.

D.Keerl, Material characterization of an engineered spider silk protein and conception of a process for its biomimetic spinning, University of Bayreuth, 2014, pp. 1-164, University of Bayreuth, Bayreuth, Germany.

Yong-Woo Lee, Silk reeling and testing manual, FAO Agricultural Services Bulletin, 1999, No. 136, Food and Agriculture Organization, Rome, Italy.

F.Bisaccia et al, Migration of monocytes in the presence of elastolytic fragments of elastin and in synthetic derivates, International Journal of Peptide & Protein Research, 1994, vol. 44, pp. 332-341, Munksgaard, Belgium.

Douglas A. Horton et al, Cyclic tetrapeptides via the ring contraction strategy: chemical techniques useful for their identification, Organic & Biomolecular Chemistry, 2008, vol. 6, pp. 1386-1395, The Royal Society of Chemistry, London, United Kingdom.

CAS Registry No. 5519-72-2 Cyclo(L-alanyl-L-alanyiglycylglycyl-L-alanyiglyeyl) Supply & Price list, 1984, Guide Chem, Hangzhou, China.

Ji An Joung et al, Application of Food-Grade Proteolytic Enzyme for the Hydrolysis of Regenerated Silk Fibroin from Bombyx mori, Hindawi Journal of Chemistry, 2018, Article ID 12858923, pp. 1-9, Hindawi Journal of Chemistry, London, United Kingdom.

* cited by examiner

PEPTIDE FOR IMPROVING MEMORY AND PREVENTING OR ALLEVIATING COGNITIVE DYSFUNCTION, COMPOSITION COMPRISING THE SAME, AND METHOD FOR PRODUCING THE SAME

CROSS-REFERENCE TO RELATED APPLICATION

This application claims priority from and the benefit of Korean Patent Application No. 10-2019-0128320, filed on Oct. 16, 2019, No. 10-2019-0141469, filed on Nov. 7, 2019, No. 10-2019-0144273, filed on Nov. 12, 2019, No. 10-2019-0144275, filed on Nov. 12, 2019, No. 10-2019-0144448, filed on Nov. 12, 2019, No. 10-2019-0144499, filed on Nov. 12, 2019, No. 10-2019-0150276, filed on Nov. 21, 2019, No. 10-2019-0153393, filed on Nov. 26, 2019, No. 10-2019-0160472, filed on Dec. 5, 2019, No. 10-2019-0162437, filed on Dec. 9, 2019, No. 10-2019-0162438, filed on Dec. 9, 2019, No. 10-2019-0131513, filed on Oct. 22, 2019, No. 10-2019-0160478, filed on Dec. 5, 2019, No. 10-2019-0162439, filed on Dec. 9, 2019, No. 10-2019-0133333, filed on Oct. 25, 2019, No. 10-2019-0134292, filed on Oct. 28, 2019, No. 10-2019-0160480, filed on Dec. 5, 2019, No. 10-2019-0134293, filed on Oct. 28, 2019, No. 10-2019-0160484, filed on Dec. 5, 2019, No. 10-2019-0162441, filed on Dec. 9, 2019, which is hereby incorporated by reference for all purposes as if set forth herein.

BACKGROUND

Field

The present disclosure relates to a peptide for improving memory and preventing or ameliorating cognitive dysfunction, a composition comprising the same, and a method for producing the same. More particularly, the present disclosure provides a peptide for improving memory and preventing or ameliorating cognitive dysfunction, and a composition comprising the same. Moreover, the present disclosure provides a method capable of providing a peptide composition for improvement of memory and prevention or alleviation of cognitive dysfunction by enzymatic hydrolysis of silk fibroin.

Discussion of the Background

Currently, in the field of functional materials, in addition to methods for finding new materials, active ingredients required for existing materials are specified, purified and separated so that they can be provided in a form suitable for the needs.

Silk cocoon is composed of the fibrous protein fibroin and the gum-like protein sericin surrounding the fibroin. Silk protein amino acids include glycine, alanine, sericine and tyrosine, which are major amino acids accounting for 90% or more. In recent years, development has been actively made to use these proteins as materials for functional foods or beverages. However, in the techniques known to date, silk proteins collected from silk cocoons have been used intact without being subjected to a separate treatment process, or a method of purifying an aqueous solution of fibroin by dialysis has been used. Thus, when the silk protein is produced by mass production, the yield of production is uneconomically low. In addition, the silk protein has problems in that, due to the fibrous structural feature and amino acid sequence of the silk protein, degradation of the silk protein in the human body is delayed or difficult and the absorption rate of the silk protein in the human body is low, and hence the value of the silk protein as a functional food material is degraded.

Known techniques for producing silk amino acids are broadly divided into an acid hydrolysis method and an enzymatic degradation method. In Japan, this silk protein is hydrolyzed by an acid, alkali or enzyme into low-molecular-weight peptides or amino acids which are easily digested and absorbed when eating. In the enzymatic degradation method among the techniques, an enzymatic protein is involved in specific binding and cleaves the chains of the silk protein, and thus the degradation rate of the silk protein into amino acids is very low, whereas, in the acid hydrolysis method, almost all of the silk protein is degraded into amino acids or peptides. From the viewpoint of an actual mass production process, the enzymatic degradation method has a simple process, but shows a low yield due to low degradation rate, and the human body absorption rate of the produced amino acids is low, whereas the silk amino acids produced by the acid hydrolysis method shows a human body absorption rate of about 90% so as to be effective for absorption in the human body, and contain larger amounts of functional amino acids useful for the human body.

The method for acid hydrolysis of silk protein, proposed in the present disclosure, is a new method capable of producing a product which is more advantageous in terms of the amino acid composition of an acid hydrolydate and the content of functional components showing physiological activity.

In the market of functional peptides produced by hydrolysis of protein sources and their research and development, Japan is currently the most advanced country, but the scope of application of peptide foods remains limited, and the market is also in the forming stage. It is known that functional peptide foods currently commercialized in Japan are still being studied on the functionality of promotion of digestion and absorption, the protein molecular weight distribution and digestion of silk hydrolyzate, the inhibitory effect of silk fibroin on serum cholesterol, the importance of sulfur amino acids in metabolism of cholesterol, the promotion of calcium absorption, the prevention of osteoporosis, the functionality of inhibition of alcohol absorption, hypertension prevention functionality, antioxidant functionality, anti-allergic functionality, and the like.

In addition, as studies on other functionalities of silk fibroin, studies on the application of silk protein to foam food processing and the application of silk fabric residue as a food material have also been reported. However, these studies on physiological activities have not been systematically conducted, but have been conducted merely to confirm the activities (antidiabetic activity, alcohol metabolism promotion activity, cholesterol lowering activity, etc.) of hydrolysates after administration to animals or to evaluate whether activities that can be exhibited by major amino acids can also be exhibited by hydrolysates. The functionalities of the product proposed in the present disclosure include anticancer activity, anti-genotoxicity, etc., which inhibit genetic damage.

Meanwhile, dementia is a complex clinical syndrome that generally shows a marked impairment in human cognitive function, intellectual ability, emotion, and behavioral changes, and is a condition in which impairment in cerebral cortex functions such as memory, attention, language function, visuospatial function, etc. occurs, causing great difficulty in daily life and social life. Dementia is defined as a case in which there is impairment in one or more of different cognitive functions, including memory, and a case in which only memory is impaired is not called dementia.

Dementia is caused by various etiologies, including degenerative brain diseases such as Alzheimer's disease or Parkinson's disease, brain hemorrhage, metabolic diseases such as hepatic encephalopathy or Wilson's disease, infectious diseases neurosyphilis or AIDS, drug addiction such as alcoholism, and brain trauma, and any disease that can cause structural or functional abnormalities in the central nervous system can cause dementia. Among them, dementia caused by Alzheimer's disease is the most common at 50 to 60%, followed by dementia caused by cerebrovascular diseases.

Memory cognitive impairment is the first symptom suffered by Alzheimer's disease patients and is also the most common symptom. Patients who are in the early stage of Alzheimer's disease suffer from a recent memory impairment that is unable to memorize recent conversations or details of work, due to damage to the hippocampal neurons and the loss of ability to store recent memories. However, during this stage, remote long-term memory of events in the distant past is relatively well maintained. However, as the disease progresses, the cerebral cortex associated with the storage of long-term memory is damaged, and these memories of the past gradually become impaired.

SUMMARY

It is an object of the present disclosure to provide a peptide having an excellent effect of improving cognitive function, particularly an excellent effect of improving cognitive function in an early stage, a composition comprising the same, and a method for producing the same.

The present disclosure is intended to provide a peptide composition for improving memory and preventing or ameliorating cognitive dysfunction, which has an excellent activity of improving memory and alleviating cognitive dysfunction, particularly an excellent effect of improving cognitive function in an early stage.

The present disclosure is intended to provide a method for a silk-derived peptide, which is capable of more effectively producing the silk-derived peptide using a hydrolase.

According to the present disclosure, it is possible to miniaturize an existing process system while maintaining the same production of a final product, and it is possible to produce a silk-derived peptide with a high yield within a short time by a small process.

To achieve the above object, a peptide according to one embodiment of the present disclosure may comprise the amino acid sequence represented by any one of the following Formulas 1 to 5:

Tyr-Gly-$X_1$—$X_2$      [Formula 1]

wherein $X_1$ is Ala, Tyr, Thr, Val, Gly, Ile or Gln, and $X_2$ is Ala, Tyr, Ile, Val or Gly;

Ile-Gly-$Z_1$—$Z_2$      [Formula 2]

wherein $Z_1$ is Ala, Tyr, Val or Gln, and $Z_2$ is Ala, Tyr, Val or Gly;

Ile-Gly-Val-$a_1$-$a_2$      [Formula 3]

wherein $a_1$ is Ala, Tyr or Val, and $a_2$ is Ala, Tyr, Thr, Val, Gly or Gln;

$a_1$-Gly-Gly-$a_1$      [Formula 4]

wherein $a_1$ is Ala, Tyr, or Val;

$a_1$-Gly-Gly-$a_1$-Gly-$a_2$      [Formula 5]

wherein $a_1$ is Ala, Tyr or Val, and $a_2$ is Ala, Tyr, Ile or Val.

A peptide composition for improving memory and preventing or alleviating cognitive dysfunction according to another embodiment of the present disclosure may comprise the peptide.

The composition may be derived from silk fibroin.

A method for producing a peptide for improving memory and preventing or alleviating cognitive dysfunction according to still another embodiment of the present disclosure may comprise steps of: dissolving silk fibroin; hydrolyzing the dissolved silk fibroin by treatment with an enzyme mixture comprising a first protease, which comprises bromelain, and a second protease comprising any one selected from the group consisting of Flavourzyme, Protamex, neutrase, Veron W, Sumizyme, zingibain, calpain, protease NP, validase, and mixtures thereof; and removing the proteases.

A method for producing a peptide for improving memory and preventing or alleviating cognitive dysfunction according to yet another embodiment of the present disclosure may comprise steps of: dissolving silk fibroin; hydrolyzing the dissolved silk fibroin by treatment with a protease comprising any one selected from the group consisting of Flavourzyme, papain, Protamex, neutrase, Veron W, Sumizyme, zingibain, calpain, protease NP, validase, and mixtures thereof; and removing the protease.

A method for producing a peptide for improving memory and preventing or alleviating cognitive dysfunction according to still yet another embodiment of the present disclosure may comprise steps of: dissolving silk fibroin; hydrolyzing the dissolved silk fibroin by treatment with a protease comprising any one selected from the group consisting of delvorase, chymotrypsin, subtilisin, actinidin, lactoferrin, kokulase P, keratinase, cathepsin K, and mixtures thereof; and removing the protease.

In method for producing a peptide for improving memory and preventing or alleviating cognitive dysfunction, the protease may further comprise Umamizyme.

In method for producing a peptide for improving memory and preventing or alleviating cognitive dysfunction, the protease may further comprise ficin.

In method for producing a peptide for improving memory and preventing or alleviating cognitive dysfunction, the step of dissolving silk fibroin may comprise dissolving silk fibroin powder, and the silk fibroin powder may be produced by mixing silk fibroin and glycerin and grinding the mixture, followed by washing with water, filtration and drying.

The cognitive dysfunction may be selected from the group consisting of dementia, learning disability, agnosia, forgetfulness, aphasia, ataxia, delirium, AIDS-induced dementia, Binswanger's disease, Lewy's body dementia, frontotemporal dementia, mild cognitive impairment, multiple infarct dementia, Pick's disease, semantic dementia, Alzheimer's dementia, and vascular dementia.

Hereinafter, the present disclosure will be described in more detail.

The term "silk" refers to a fiber obtained from cocoons made by silkworms, and collectively refers to products made from silk as a raw material. In a broad sense, the term "silk" also includes product produced by spinning of wild silk such as tussah silk as a raw material. True silk, commonly referred to as silk, is also referred to as cultivated or domestic silk. Meanwhile, the cocoon referred to in the present disclosure is defined as a concept including silk.

Silk fiber is composed of fibroin and sericin, and also contains small amounts of encephaloid matter, fatty matter and inorganic salts. The constituents of silk are fibroin and sericin, which are fibrous proteins. Silk is composed of a biopolymer in its natural state. Compounds having a molecular weight of 10,000 or more are in the form of fibers, membranes or lumps. Silk is a polymeric protein, which consists of amino acids, which are composed of simple alpha amino acids comprising an amino group ($-NH_2$) and carboxyl group ($-COOH$) bonded to carbon.

In addition, a polymer comprising a large number of amino acids chained together in a beaded shape is referred to as a polypeptide. Eventually, $-NH_2$ and $-COOH$ of two amino acids react together to remove water ($H_2O$), and the amino acids are arranged in parallel to form a peptide.

The amino acids that make up fibroin are rich in glycine (side chain—H) and alanine ($-CH_3$), and these amino acids are characterized by a short side chain of the molecule. In addition, the sum of these amino acids and serine (side chain-$CH_2OH$) and tyrosine (side chain-$CH(OH)CH_2$) is more than 90%. Furthermore, the amino acid composition of fibroin differs from that of sericin in that the contents of acidic amino acids (aspartic acid and glutamic acid) and excitatory amino acids (lysine, alanine and histidine) are small. When these amino acids are bonded together in different combinations, a polypeptide is formed. Fibroin is hydrolyzed into amino acids, and alpha-amino acids having a molecular weight of from 300 to 500,000 or 3,000 to 3,500 are bonded together to form a single-stranded molecule.

As used herein, the term "silk-derived peptide" refers to a peptide produced by hydrolyzing silk-derived fibroin to have a certain amino acid sequence and a size sufficient to be absorbed in vivo.

In addition, the term "silk-derived peptide", as used herein, may also refer to a silk protein and may be used in the same sense.

Preferably, the method for producing the silk-derived peptide may further comprise, before the step of dissolving silk fibroin, a sericin removal step of mixing cocoons with purified water and removing sericin by heat treatment to obtain silk fibroin.

The sericin removal step refers to a step of removing the sericin covering the silk fibroin. Since sericin contains polar amino acids, it is generally removed by heat treatment after mixing with purified water. In particular, the efficiency of the process of sericin removal increases as the sericin removal step is performed at a higher temperature, but if the sericin removal step is performed at a temperature higher than 97° C., a problem may arise in that the loss of fibroin occurs, and hence the temperature cannot be increased indefinitely.

In the method for producing the silk fibroin-derived fibroin, the sericin removal step may comprise adding a thickener and an additive and performing heat treatment at 30 to 70° C.

In the sericin removal step, when the heat treatment is performed at 30 to 70° C. in the presence of the thickener and the additive, the sericin removal process may be much faster than when the viscosity is not increased at the same temperature while heat treatment is performed. In particular, when the viscosity is increased, there is an advantage in that the loss of fibroin does not occur.

In the method for producing the silk fibroin-derived fibroin, the mixture of cocoon and purified water in the sericin removal step may have a viscosity of 1.2 to 120 cP. When the mixture is within the above viscosity range, there are advantages in that not only can sericin be quickly removed in the sericin removal process, but there is little loss of fibroin.

Preferably, in the method for producing the silk fibroin-derived fibroin, the mixture of cocoons and purified water the sericin removal step may have a viscosity of 1.3 to 40 cP, and the sericin removal step may comprise: a first heat-treatment step of heat-treating the mixture at 98 to 100° C. for 2 to 10 minutes; and a second heat-treatment step of heat-treating the mixture at 30 to 40° C.

The temperature of the first heat-treatment step is the temperature at which fibroin is dissolved, but when heat-treatment of the mixture is initiated after the viscosity of the mixture of cocoons and purified water is adjusted to 1.3 to 40 cP, the loss of fibroin may not occur.

When the second heat-treatment step is subsequently performed at a relatively low temperature, sericin may be quickly removed.

If the viscosity of the mixture of cocoons and purified water in the first heat treatment step is less than 1.3 cP, a problem may arise in that that rapid loss of fibroin occurs. On the other hand, if the viscosity is higher than 40 cP, the effect of improving the sericin removal process may not appear despite the first heat-treatment step.

Therefore, when the first heat-treatment and second heat-treatment steps are performed while the above-described viscosity range is maintained, it is possible to increase the efficiency of the sericin removal process, because the loss of fibroin does not occur while sericin is more effectively removed.

When the additive is included, it is possible to not only minimize the loss of fibroin, but also increase the yield of a fibroin hydrolysate, i.e., a silk fibroin-derived peptide, which exhibits the effect of improving memory and cognitive function, in a subsequent step.

Preferably, the additive comprises xylanase, and may comprise, based on 100 parts by weight of xylanase, 10 to 100 parts by weight of sorbitol, 1 to 10 parts by weight of mannitol, and 0.1 to 5 parts by weight of galactose.

When this additive is used, the loss of fibroin in the sericin removal step may decrease, the yield of the silk fibroin-derived peptide having a cognitive function improvement effect in the hydrolysis step may increase, and the efficiency of improving cognitive function and memory may be improved.

The step of dissolving silk fibroin is a step of preparing a mixture of silk fibroin with purified water, an organic solvent or other liquid.

The hydrolysis step is a step of hydrolyzing the dissolved silk fibroin by treatment with an enzyme mixture comprising a first protease, which comprises bromelain, and a second protease comprising any one selected from the group consisting of Flavourzyme, Protamex, neutrase, Veron W, Sumizyme, zingibain, calpain, protease NP, validase, and mixtures thereof Preferably, the protease may be any one selected from the group consisting of bromelain, zingibain, calpain, and mixtures thereof. When this protease is used, it is possible to produce a silk fibroin peptide having a high effect of improving cognitive function and memory.

More preferably, the protease may be an enzyme mixture comprising bromelain and comprising, based on 100 parts by weight of bromelain, 10 to 50 parts by weight of zingibain and 5 to 30 parts by weight of calpain. When this protease is used, the produced silk fibroin peptide may not only have an excellent effect on cognitive function and memory improvement, but also exhibit a significantly increased effect of improving cognitive function and memory within a short period of time. Therefore, it is possible to produce a silk fibroin peptide capable of exhibiting the effect of improving cognitive function and memory within a short period of time.

Preferably, the protease may be an enzyme mixture comprising bromelain and, based on 100 parts by weight of bromelain, 10 to 50 parts by weight of zingibain, 5 to 30 parts by weight of calpain, and 1 to 20 parts by weight of Umamizyme. When this protease is used, the absorption rate of the hydrolysate and the activity of the active ingredient (silk derived peptide) on cognitive function improvement may significantly increase. Thus, a silk-derived peptide having these effects may be produced.

Preferably, the protease may be any one selected from the group consisting of papain, zingibain, calpain, and mixtures thereof. When this protease is used, it is possible to produce a silk fibroin peptide having a high effect of improving cognitive function and memory.

More preferably, the protease used may be an enzyme mixture comprising papain and, based on 100 parts by weight of papain, 10 to 50 parts by weight of zingibain and 5 to 30 parts by weight of calpain. When this protease is used, the produced silk fibroin peptide may not only have an excellent effect on cognitive function and memory improvement, but also exhibit a significantly increased effect of improving cognitive function and memory within a short period of time. Therefore, it is possible to produce a silk fibroin peptide capable of exhibiting the effect of improving cognitive function and memory within a short period of time.

Preferably, the protease used may be an enzyme mixture comprising papain and based on 100 parts by weight of papain, 10 to 50 parts by weight of papain, 10 to 50 parts by weight of zingibain, 5 to 30 parts by weight of calpain, and 1 to 20 parts by weight of Umamizyme. When this protease is used, the absorption rate of the hydrolysate and the activity of the active ingredient (silk derived peptide) on cognitive function improvement may significantly increase. Thus, a silk-derived peptide having these effects may be produced.

Preferably, the protease may be any one selected from the group consisting of actinidin, kokulase P, keratinase, and mixtures thereof. When this protease is used, it is possible to produce a silk fibroin peptide having a high effect of improving cognitive function and memory.

More preferably, the protease used may be an enzyme mixture comprising actinidin and, based on 100 parts by weight of actinidin, 5 to 20 parts by weight of kokulase P and 5 to 20 parts by weight of keratinase. When this protease is used, the produced silk fibroin peptide may not only have an excellent effect on cognitive function and memory improvement, but also exhibit a significantly increased effect of improving cognitive function and memory within a short period of time. Therefore, it is possible to produce a silk fibroin peptide capable of exhibiting the effect of improving cognitive function and memory within a short period of time.

Preferably, the protease used may be an enzyme mixture comprising actinidin and, based on 100 parts by weight of actinidin, 5 to 20 parts by weight of kokulase P, 5 to 20 parts by weight of keratinase, and 1 to 5 parts by weight of cathepsin K. When this protease is used, the absorption rate of the hydrolysate and the activity of the active ingredient (silk derived peptide) on cognitive function improvement may significantly increase. Thus, a silk-derived peptide having these effects may be produced.

More preferably, the protease used may be an enzyme mixture comprising ficin and, based on 100 parts by weight of ficin, 5 to 20 parts by weight of kokulase P and 5 to 20 parts by weight of keratinase. When this protease is used, the produced silk fibroin peptide may not only have an excellent effect on cognitive function and memory improvement, but also exhibit a significantly increased effect of improving cognitive function and memory within a short period of time. Therefore, it is possible to produce a silk fibroin peptide capable of exhibiting the effect of improving cognitive function and memory within a short period of time.

Preferably, the protease used may be an enzyme mixture comprising ficin and based on 100 parts by weight of ficin, 5 to 20 parts by weight of kokulase P, 5 to 20 parts by weight of keratinase and 1 to 5 parts by weight of cathepsin K. When this protease is used, the absorption rate of the hydrolysate and the activity of the active ingredient (silk derived peptide) on cognitive function improvement may significantly increase. Thus, a silk-derived peptide having these effects may be produced.

The step of removing the protease refers to a step of removing the proteases or the activity of the proteases after the hydrolysis step, and is defined to include all types that may be used by those skilled in the art.

In addition, the step of removing the protease may be a step of removing the activity of the protease by heat treatment.

In the method for producing a silk-derived peptide, the silk-derived peptide may be for improving memory.

The silk fibroin powder may be produced by mixing silk fibroin and glycerin and grinding the mixture, followed by washing with water, filtration and drying.

The silk fibroin may be treated with low-temperature plasma.

When the silk fibroin powder is used, much smaller amounts of calcium chloride and water compared to those in a conventional art may be used in the step of dissolving silk fibroin, and silk fibroin may be dissolved at a relatively low temperature. Accordingly, not only can the process required to use the silk-derived peptide be miniaturized, but also the amount of water used can be reduced.

Specifically, in the conventional art, silk fibroin is dissolved in a calcium chloride solution, followed by hydrolysis. Thus, the calcium chloride solution used as a solvent to dissolve silk fibroin is usually about 5 to 10 times the amount of silk fibroin. In addition, the dissolution of silk fibroin is also performed at a relatively high temperature of 80 to 110° C.

However, when the silk fibroin powder is used, the calcium chloride solvent may be used in an amount equal to 0.8 to 1.3 times the mass of the silk fibroin powder to dissolve the silk fibroin powder. In addition, the reaction for dissolution may be performed at a relatively low temperature of 40 to 60° C. As a result, the amounts of the reactants may be reduced, so that the process may be miniaturized. In addition, since the amount of calcium chloride solution used is reduced, the amount of water used to remove the salt may be reduced and the time required for the process of removing the salt may be shortened. Therefore, it is possible to produce the same amount of a silk-derived peptide as a final product within a shorter time by the use of a much smaller reactor. Thus, the process may have excellent efficiency.

Specifically, for preparation of the silk fibroin powder, glycerin is mixed with silk fibroin from which sericin has been removed. Then, the mixture is ground, washed with water, filtered, and dried. The silk fibroin powder itself prepared by the above method may have a certain solubility.

In addition, silk fibroin from which sericin has been removed may be treated with low-temperature plasma at atmospheric pressure, thereby modifying the surface of the silk fibroin material, and mixed with glycerin, and the mixture may be washed with water, filtered, and dried. The silk fibroin powder prepared by this method may have better solubility.

Common silk fibroin is insoluble in water, but the silk fibroin powder prepared by the above method has a solubility of about 30% or more in water. In addition, unlike when common silk fibroin is used, even when a much lower amount of the calcium chloride solution is used, silk fibroin may be completely dissolved.

In the method for producing a silk-derived peptide, the silk-derived peptide may be for preventing or alleviating cognitive dysfunction.

The cognitive dysfunction may be selected from the group consisting of dementia, learning disability, agnosia, forgetfulness, aphasia, ataxia, delirium, AIDS-induced dementia, Binswanger's disease, Lewy's body dementia, frontotemporal dementia, mild cognitive impairment, multiple infarct dementia, Pick's disease, semantic dementia, Alzheimer's dementia, and vascular dementia.

A food for improving cognitive function and memory according to another embodiment of the present disclosure may comprise a silk-derived peptide produced according to the method for producing a silk-derived peptide.

As used herein, the expression "improving cognitive function and memory" not only means simply restoring or improving impaired cognitive function and memory, but also is defined to include preventing or alleviating cognitive function and memory impairments caused by brain neurological disease.

A medicament for preventing and alleviating brain neurological disease according to still another embodiment of the present disclosure may comprise a silk-derived peptide produced according to the method for producing a silk-derived peptide.

As used herein, the term "brain neurological disease" is defined to include all neurodegenerative diseases such as dementia, Huntington's disease, Parkinson's disease and amyotrophic lateral sclerosis, diseases caused by ischemia or reperfusion, such as ischemic stroke, and mental diseases such as schizophrenia and post-traumatic stress disorder.

A peptide according to one embodiment of the present disclosure may be represented by the following Formula 1:

$$\text{Tyr-Gly-}X_1\text{—}X_2 \qquad \text{[Formula 1]}$$

wherein $X_1$ is Ala, Tyr, Thr, Val, Gly, Ile or Gln, and $X_2$ is Ala, Tyr, Ile, Val or Gly.

In the present disclosure, it was found that, when silk fibroin was hydrolyzed using a combination of specific proteases and the produced silk fibroin-derived peptide included a specific amino acid sequence, the silk fibroin-derived peptide not only exhibited the effect of improving cognitive function and memory, but also exhibited the effect of improving cognitive function and memory within a very short period of time. Based on this finding, specific analysis was performed to identify an amino acid sequence exhibiting a fast action and effect, unlike a common hydrolysate.

Accordingly, the corresponding hydrolysates were analyzed, and as a result, it was assumed that a peptide or a peptide composition, such as a peptide comprising the amino acid sequence of Formula 1, or a peptide composition comprising a mixture of the peptide comprising the amino acid sequence of Formula 1 and a peptide comprising the amino acid sequence of Formula 2, would exhibit the above-described effect. Based on this assumption, an experiment was performed, and as a result, it was confirmed that the above-described peptide or peptide composition not only exhibited a high effect of improving cognitive function and memory, but also exhibited the effect of improving cognitive function and memory within a very short period of time.

Preferably, the peptide comprising the amino acid sequence of Formula 1 may be any one of P1-1 to P1-6 as shown in Table 1 below.

TABLE 1

| Peptides | Amino acid sequences |
|---|---|
| P1-1 | Tyr-Gly-Gln-Gly |
| P1-2 | Tyr-Gly-Gly-Ala |
| P1-3 | Tyr-Gly-Ala-Ala |
| P1-4 | Tyr-Gly-Val-Gly |
| P1-5 | Tyr-Gly-Val-Ile |
| P1-6 | Tyr-Gly-Ile-Ala |

More preferably, the peptide of Formula 1 may be the peptide P1-2, P1-3, P1-5 or P1-6 shown in Table 1 above. This peptide may not only have an excellent effect of improving cognitive function and memory, but also have a very excellent effect in an early effect, and thus may exhibit an effect of improving cognitive function and memory within a short period of time.

In particular, the peptide P1-5 or P1-6 may not only have an excellent effect of improving cognitive function and memory, but also exhibit an effect of improving cognitive function and memory within a shorter period of time.

A peptide according to another embodiment of the present disclosure may be represented by the following Formula 2:

$$\text{Ile-Gly-}Z_1\text{—}Z_2 \qquad \text{[Formula 2]}$$

wherein $Z_1$ is Ala, Tyr, Val or Gln, and $Z_2$ is Ala, Tyr, Val or Gly.

A peptide composition according to still another embodiment of the present disclosure may comprise: the peptide comprising the amino acid sequence represented by Formula 1; and the peptide comprising the amino acid sequence represented by Formula 2.

Preferably, the peptide represented by Formula 2 may be any one of P2-1 to P2-4 as shown in Table 2 below.

TABLE 2

| Peptides | Amino acid sequences |
|---|---|
| P2-1 | Ile-Gly-Tyr-Val |
| P2-2 | Ile-Gly-Val-Ala |
| P2-3 | Ile-Gly-Ala-Tyr |
| P2-4 | Ile-Gly-Gln-Gly |

The peptide composition comprising the peptide shown in Table 2 above may not only have an excellent effect of exhibiting cognitive function and memory, but also exhibit the effect thereof within a short period of time.

Meanwhile, the peptide composition may comprise the peptide represented by Formula 2 in an amount of 50 to 80 parts by weight based on 100 parts by weight of the peptide represented by Formula 1.

A peptide according to yet embodiment of the present disclosure may be represented by the following Formula 3:

$$\text{Ile-Gly-Val-}a_1\text{-}a_2 \qquad \text{[Formula 3]}$$

wherein $a_1$ is Ala, Tyr or Val, and $a_2$ is Ala, Tyr, Thr, Val, Gly or Gln.

Preferably, the peptide comprising the amino acid sequence represented by Formula 1 may be any one of F1 to F3 as shown in Table 3 below.

TABLE 3

| Peptides | Amino acid sequences |
|---|---|
| F1 | Ile-Gly-Val-Ala-Thr |
| F2 | Ile-Gly-Val-Ala-Tyr |
| F3 | Ile-Gly-Val-Ala-Gly |

The peptides shown in Table 3 above may not only have an excellent effect of improving cognitive function and memory, but also exhibit a significantly increased effect of improving cognitive function and memory in an early stage due to the excellent activity thereof.

A peptide for improving memory and cognitive function, produced according to another embodiment of the present disclosure, comprises the amino acid represented by Formula 3 and the amino acid represented by Formula 1.

In the present disclosure, it was found that, when silk fibroin was hydrolyzed using a combination of specific proteases and the produced silk fibroin-derived peptide included a specific amino acid sequence, the silk fibroin-derived peptide not only exhibited the effect of improving cognitive function and memory, but also exhibited the effect of improving cognitive function and memory within a very short period of time. Based on this finding, specific analysis was performed to identify an amino acid sequence exhibiting a fast action and effect, unlike a common hydrolysate.

Accordingly, the corresponding hydrolysates were analyzed, and as a result, it was assumed that a peptide or a peptide composition, such as a peptide comprising the amino acid sequence of Formula 1-1, or a peptide composition comprising a mixture of the peptide comprising the amino acid sequence of Formula 1-1 and a peptide comprising the amino acid sequence of Formula 1-2, would exhibit the above-described effect. Based on this assumption, an experiment was performed, and as a result, it was confirmed that the above-described peptide or peptide composition not only exhibited a high effect of improving cognitive function and memory, but also exhibited the effect of improving cognitive function and memory within a very short period of time.

The peptide according to the present disclosure may comprise the amino acid sequence represented by the following Formula 4 or 5:

$$a_1\text{-Gly-Gly-}a_1 \quad \text{[Formula 4]}$$

wherein $a_1$ is Ala, Tyr or Val;

$$a_1\text{-Gly-Gly-}a_1\text{-Gly-}a_2 \quad \text{[Formula 5]}$$

wherein $a_1$ is Ala, Tyr or Val, and $a_2$ is Ala, Tyr, Ile or Val.

In the present disclosure, it was found that, when silk fibroin was hydrolyzed using a combination of specific proteases and the produced silk fibroin-derived peptide included a specific amino acid sequence, the silk fibroin-derived peptide not only exhibited the effect of improving cognitive function and memory, but also exhibited the effect of improving cognitive function and memory within a very short period of time. Based on this finding, specific analysis was performed to identify an amino acid sequence exhibiting a fast action and effect, unlike a common hydrolysate.

Accordingly, the corresponding hydrolysates were analyzed, and as a result, it was assumed that a peptide or a peptide composition, such as a peptide comprising the amino acid sequence of Formula 4 or 5, or a peptide composition comprising a mixture of the peptide comprising the amino acid sequence of Formula 4 or 5 and a peptide comprising the amino acid sequence of Formula 2, would exhibit the above-described effect. Based on this assumption, an experiment was performed, and as a result, it was confirmed that the above-described peptide or peptide composition not only exhibited a high effect of improving cognitive function and memory, but also exhibited the effect of improving cognitive function and memory within a very short period of time.

Preferably, the peptide comprising the amino acid sequence of Formula 4 may be any one of P4-1 to P4-3 as shown in Table 4 below. In addition, the peptide comprising the amino acid sequence of Formula 5 may be any one of P5-1 to P5-4 as shown in Table 4 below.

TABLE 4

| Peptides | Amino acid sequences |
|---|---|
| P4-1 | Ala-Gly-Gly-Ala |
| P4-2 | Tyr-Gly-Gly-Tyr |
| P4-3 | Val-Gly-Gly-Val |
| P5-1 | Tyr-Gly-Gly-Tyr-Gly-Ile |
| P5-2 | Tyr-Gly-Gly-Tyr-Gly-Val |
| P5-3 | Tyr-Gly-Gly-Tyr-Gly-Ala |
| P5-4 | Tyr-Gly-Gly-Tyr-Gly-Tyr |

More preferably, the peptide of Formula 4 may be the peptide P4-2 or P4-3 shown in Table 4 above. This peptide may not only have an excellent effect of improving cognitive function and memory, but also have a very excellent effect in an early effect, and thus may exhibit the effect of improving cognitive function and memory within a short period of time.

In particular, the peptide P4-2 may not only have an excellent effect of improving cognitive function and memory, but also exhibit an excellent effect of improving cognitive function and memory within a shorter period of time.

More preferably, the peptide of Formula 5 may be the peptide P5-1 or P5-4 shown in Table 4 above.

This peptide may have an excellent effect of improving cognitive function and memory, and may exhibit a significantly increased effect of improving cognitive function and memory in an early stage of administration.

Preferably, a peptide composition according to another embodiment of the present disclosure may comprise a peptide comprising the amino acid sequence represented by Formula 4, and may further comprise a peptide comprising the amino acid sequence represented by Formula 2.

In addition, the peptide composition according to the present disclosure may comprise a peptide comprising the amino acid sequence represented by Formula 5, and may further comprise a peptide comprising the amino acid sequence represented by Formula 2.

The peptides represented by Formulas 1 to 5 may be added after synthesis, and according to the production method of the present disclosure, a composition comprising the peptides may be produced.

This composition may quickly exhibit an activity of improving cognitive function and memory by a synergistic effect due to interaction between the peptides.

A food according to another embodiment of the present disclosure may comprise the above-described peptide or peptide composition.

A medicament for preventing or alleviating cognitive dysfunction according to still another embodiment of the present disclosure may comprise the above-described peptide or peptide composition.

The cognitive dysfunction may be selected from the group consisting of dementia, learning disability, agnosia, forgetfulness, aphasia, ataxia, delirium, AIDS-induced dementia, Binswanger's disease, Lewy's body dementia, frontotemporal dementia, mild cognitive impairment, multiple infarct dementia, Pick's disease, semantic dementia, Alzheimer's dementia, and vascular dementia.

The composition may comprise pharmaceutically acceptable carriers. Pharmaceutically acceptable carriers that are included in the composition those that are commonly used for formulation, including, but not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, oils, and the like. The pharmaceutical composition may further comprise, in addition to the above-described components, a lubricant, a wetting agent, a sweetener, a flavoring agent, an emulsifying agent, a suspending agent, a preservative, and the like.

The pharmaceutical composition may be administered orally or parenterally.

When the composition is administered orally, the protein or peptide is digested. For this reason, the composition for oral administration should be formulated so that the active agent is coated or protected from degradation in the stomach. In addition, the composition may be administered by any device capable of delivering the active ingredient to target cells.

A suitable dosage of the pharmaceutical composition may be used as a pharmaceutically effective amount, which means an amount sufficient to prevent or treat memory dysfunction, cognitive dysfunction or learning disability.

DETAILED DESCRIPTION OF THE ILLUSTRATED EMBODIMENTS

Figure 1:
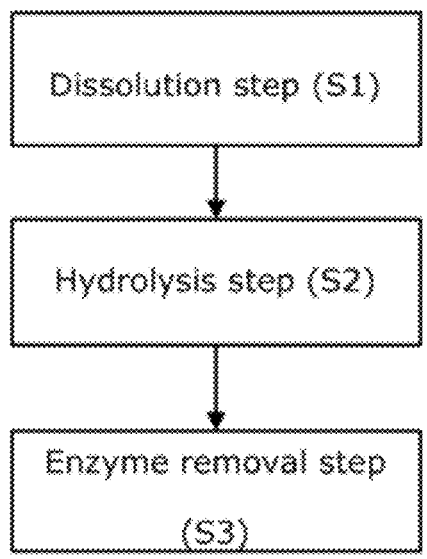
FIG. 1 is a flow chart of a method for producing a silk-derived peptide according to one embodiment of the present disclosure.

Hereinafter, examples of the present disclosure will be described in detail so that the present disclosure can be easily carried out by those skilled in the art. However, the present disclosure may be embodied in a variety of different forms and is not limited to the examples described herein Preparation Example 1

Production of Silk-Derived Peptides

Dissolved silk fibroin was mixed with purified water, treated with 1 wt % of each of the protease compositions T1 to T11 shown in Table 5 below, and hydrolyzed for 5 hours. Thereafter, the mixtures were heat-treated for 10 minutes to remove the activities of the enzymes, and then freeze-dried to obtain the powders shown in Tables 6 below.

TABLE 5

(unit: parts by weight)

| | T1 | T2 | T3 | T4 | T5 | T6 | T7 | T8 | T9 | T10 | T11 |
|---|---|---|---|---|---|---|---|---|---|---|---|
| Flavourzyme | 100 | — | — | — | — | — | — | — | — | — | — |
| Protamex | — | 100 | — | — | — | — | — | — | — | — | — |
| Bromelain | — | — | 100 | 100 | 100 | 100 | 100 | 100 | 100 | 100 | 100 |
| Zingibain | — | — | — | 5 | 10 | 30 | 50 | 60 | 30 | 30 | 30 |
| Calpain | — | — | — | 5 | 10 | 20 | 30 | 40 | 20 | 20 | 20 |
| Umamizyme | — | — | — | — | — | — | — | — | 0.5 | 10 | 25 |

TABLE 6

| | NF1 | NF2 | TF1 | TF2 | TF3 | TF4 | TF5 | TF6 | TF7 | TF8 | TF9 |
|---|---|---|---|---|---|---|---|---|---|---|---|
| Treatment enzymes | T1 | T2 | T3 | T4 | T5 | T6 | T7 | T8 | T9 | T10 | T11 |

Experimental Example 1

Experiment on Effect of Improving Memory and Cognitive Function

Experimental Example 1-1: Animal Model Experiment for Cognitive Function Improvement A. Preparation of Experimental Animals Experimental animals were white male Sprague-Dawley rats (140 to 180 g, Daehan Biolink Co., Ltd.). These rats were housed in cages (4 rats per cage) in a constant environment (temperature: 25±1° C., and relative humidity: 60±10%) for one week and allowed to access water ad libitum. At this time, the feed was fed in a limited manner so that 80% of the body weight was kept. In this experiment, a total of 50 rats were used. The rats were adapted to the maze for 5 minutes a day for 3 days before training.

B. Delayed Alternation Test

A "π" shaped maze was prepared which had a total of three arms (left, right and center) and in which an automated door was placed at the entrance of each arm so that the experimenter could control the entry and exit of animals. In the first trial, the animals were adapted to the start arm. The first trial is a "forced-choice trial", in which one arm was blocked with the door and when the animal entered the other arm, the rear was blocked with the door. The animal was considered as entering the arm when all four paws passed through the entrance. The animal was allowed to eat feed in the corresponding arm for 60 seconds. The next trials were "free-choice trials", in which the animal was free to choose the direction of the arm (left or right) starting from the start arm. The animal was made to be able to eat food as a reward only when it entered the arm that entered in the previous trial and the opposite arm.

The trials were performed with delays of 5 seconds and 20 seconds, and the cut-off time of each trial was set to 60 seconds. The number of times the animal entered the forced-choice arm and the time taken to enter the arm were measured. The same procedure was performed for 9 days with 10 trials per day, followed by assessment.

C. Administration Method

The silk peptides NF1, NF2 and TF1 to TF9 were prepared into solutions, each containing 100 mg/ml of each peptide, and were administered orally. All the samples were dissolved in distilled water and administered orally.

D. Results of Cognitive Memory Assessment

Figure 2:
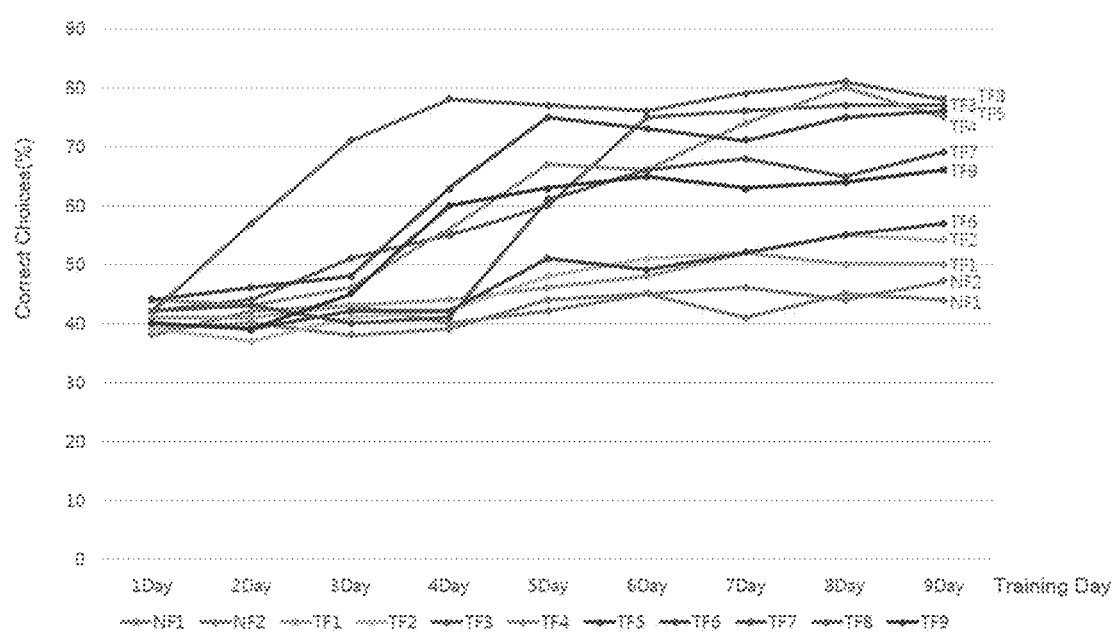
FIGS. 2, 4, 6 and 8 shows the results of performing cognitive memory assessment on silk-derived peptides produced according to the Examples of the present disclosure.

FIG. 2 shows the results of performing the T-maze test for the groups administered the silk peptides NF1, NF2 and TF1 to TF 9, respectively. FIG. 2 shows the results of performing the test with a delay of 5 seconds between the trials, and indicates that the performance was gradually improved during the training period of 9 days.

The present inventors were able to obtain results with a tendency similar to that in other experiments conducted concurrently using enzyme mixtures based on papain. Referring to FIG. 2, it could be confirmed that TF3 to TF5 and TF7 to TF9 clearly exhibited the effect of improving cognitive function. In addition, it could be seen that the peptides produced by the Preparation Example above also exhibited an excellent effect of improving cognitive function in the early stage.

In particular, it can be seen that TF8 exhibits an excellent effect of improving cognitive function in the early stage of administration, compared to the other peptides. Thus, it can be understood that, when certain amounts of peptides having specific sequences co-exist in the silk fibroin hydrolyzed by the protease mixture, they accelerate the effect of improving cognitive function, thereby exhibiting a rapid effect in the early stage of administration.

Analysis was performed to confirm this understanding, and as a result, it could be confirmed that the hydrolysates contained peptides represented by Formulas 1 to 5 as described below and the above-described acceleration effect was exhibited by these peptides.

Therefore, according to the foregoing, it is possible to provide silk-derived peptides having the effect of improving cognitive function and memory. In particular, it is possible to produce silk-derived peptides capable of accelerating the early synergistic effect on cognitive function and memory improvement and having a further increased effect of improving memory and cognitive function.

Experimental Example 1-2: Local Ischemia-Induced Animal Model

To evaluate the memory and cognitive function improvement effects of the silk-derived peptides NF1, NF2 and TF5 and TF8 produced using the proteases, an experiment on the evaluation of the effect of the peptides on the area of ischemic cerebral infarction was performed using a local ischemia-induced animal model.

A. Drug Treatment and Preparation of Local Ischemia-Induced Animal Model

A local ischemia-induced animal model was prepared using white male Sprague-Dawley rats weighing 200 to 250 g. As drugs, 1 g/kg of each of NF1, NF2, TF5 and TF8 was administered orally once 1 hour before or after induction of ischemia (oral administration group, n=6). To an ischemia control group (n=6), BG101 was administered at the same dose as that of the drug treatment group. Experimental animals were anesthetized by intramuscular injection of 30 to 40 mg/kg of ketamine, and then the skin of the neck was incised and the common carotid artery, external carotid artery, and internal carotid artery were separated from the surrounding tissue. First, the superior parathyroid gland and posterior fossa, which are branches of the external carotid artery, and pterygopalatine, which is a branch of the internal carotid artery, were electrocauterized, and the external carotid artery were cut. Then, occlusion of origin of middle cerebral artery was performed by incorporating 4-0 nylon thread (ETHICON, INC, US) into the internal carotid artery through the external carotid artery, and placing 16 to 18 mm of the nylon thread within the common carotid artery.

B. Experiment on Effect of Peptides on Decrease in Area of Ischemic Cerebral Infarction 6 hours after induction of ischemia, the heads of the animals were cut and the brains were dissected. The dissected brains were sectioned at intervals of 2 mm from the anterior pole, and incubated with 2% triphenyl tetrazolium chloride (TTC, Sigma) solution at 37° C. for 30 minutes, followed by fixing using 4% paraformaldehyde (Sigma). The stained tissue sections were imaged, and the area of a region turned white due to the occurrence of cerebral infarction, unlike a red-stained normal region, in each of the images, was measured using the MCID image processing system (Imaging Research Inc.). The ratio of the area of cerebral infarction to the total area of each brain section was calculated and then averaged. In addition, the ratio of the volume of the cerebral infarction region to the total volume of each brain section was measured. The results are shown in FIG. 3.

Figure 3:
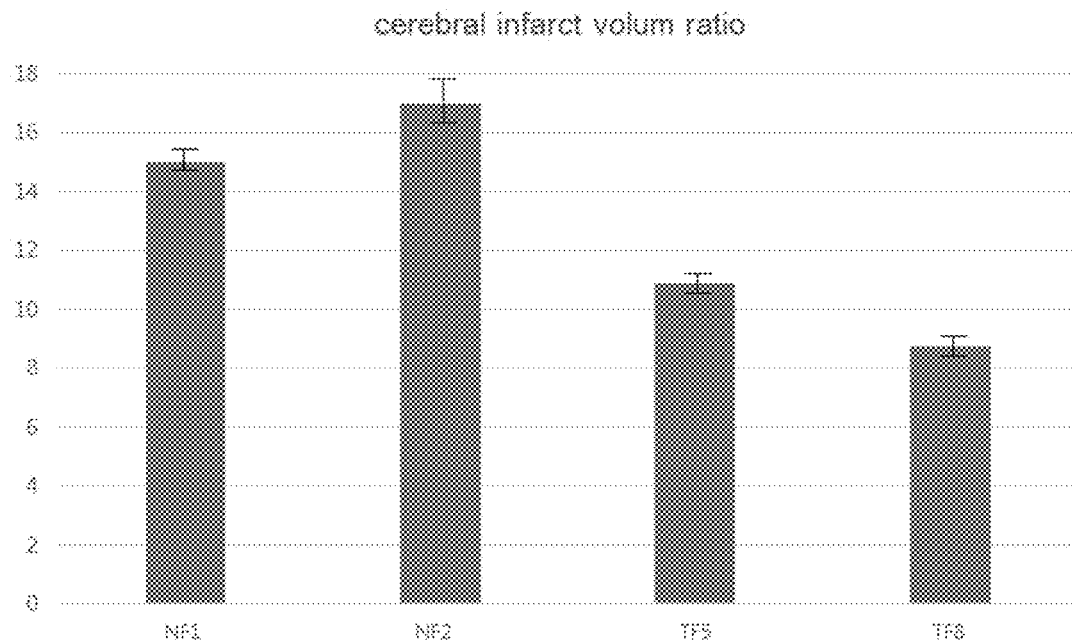
FIGS. 3, 5, 7 and 9 show the results of evaluating the effects of silk-derived peptides, produced according to the examples of the present disclosure, on ischemic cerebral infarction areas.

Referring to FIG. 3, it can be confirmed that the silk fibroin-derived peptides provided in the present disclosure can reduce the cerebral infarction region.

Preparation Example 2

Production of Silk-Derived Peptides

Dissolved silk fibroin was mixed with purified water, treated with 1 wt % of each of the protease compositions T1 to T11 shown in Table 7 below, and hydrolyzed for 5 hours. Thereafter, the mixtures were heat-treated for 10 minutes to remove the activities of the enzymes, and then freeze-dried to obtain the powders shown in Tables 8 below.

TABLE 7

(unit: parts by weight)

| | T1 | T2 | T3 | T4 | T5 | T6 | T7 | T8 | T9 | T10 | T11 |
|---|---|---|---|---|---|---|---|---|---|---|---|
| Flavourzyme | 100 | — | — | — | — | — | — | — | — | — | — |
| Protamex | — | 100 | — | — | — | — | — | — | — | — | — |
| Papain | — | — | 100 | 100 | 100 | 100 | 100 | 100 | 100 | 100 | 100 |
| Zingibain | — | — | — | 5 | 10 | 30 | 50 | 60 | 30 | 30 | 30 |
| Calpain | — | — | — | 5 | 10 | 20 | 30 | 40 | 20 | 20 | 20 |
| Umamizyme | — | — | — | — | — | — | — | — | 0.5 | 10 | 25 |

TABLE 8

| | NF1 | NF2 | NF3 | NF4 | NF5 | NF6 | NF7 | NF8 | NF9 | NF10 | NF11 |
|---|---|---|---|---|---|---|---|---|---|---|---|
| Treatment enzymes | T1 | T2 | T3 | T4 | T5 | T6 | T7 | T8 | T9 | T10 | T11 |

Experimental Example 2

Experiment on Effect of Improving Memory and Cognitive Function

Experimental Example 2-1: Animal Model Experiment for Cognitive Function Improvement According to the same methods as described in Experimental Example 1-1 above, the following experiments were performed: A. Animal model experiment on cognitive function improvement; B. Delayed alternation test; C. Administration method; and D. Results of cognitive memory assessment.

Figure 4:
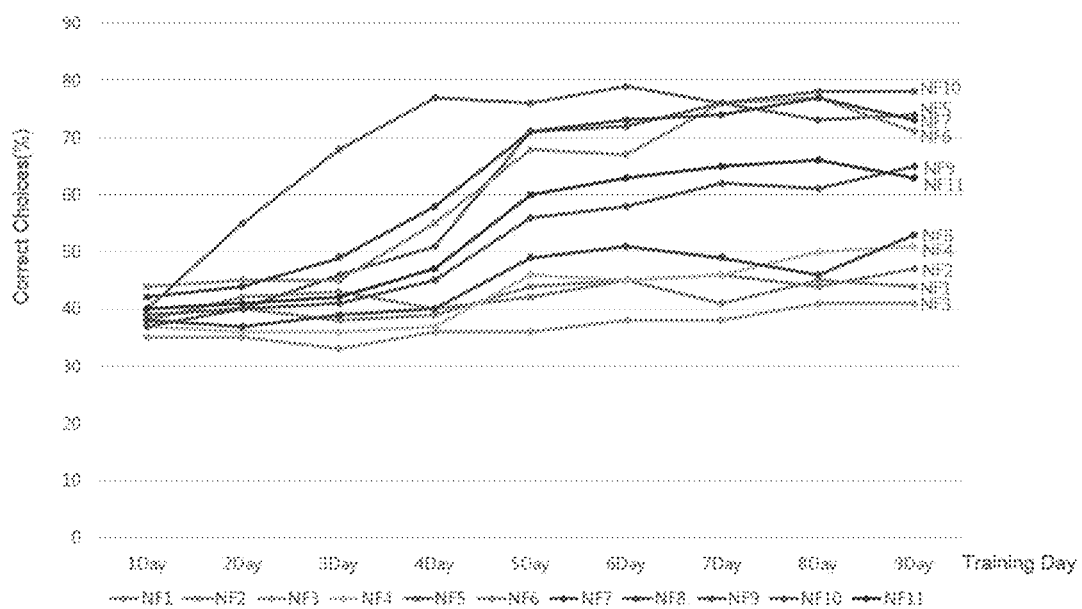

FIG. 4 shows the results of performing the T-maze test for the groups administered the silk peptides NF1 to NF11, respectively. FIG. 4 shows the results of performing the test with a delay of 5 seconds between the trials, and indicates that the performance was gradually improved during the training period of 9 days.

Referring to FIG. 4, it could be confirmed that NF5 to NF7 and NF9 to NF11 clearly exhibited the effect of improving cognitive function. In addition, it could be seen that the peptides produced by the Preparation Example above also exhibited an excellent effect of improving cognitive function in the early stage.

In particular, it can be seen that NF10 exhibits an excellent effect of improving cognitive function in the early stage of administration, compared to the other peptides. Thus, it can be understood that, when certain amounts of peptides having specific sequences co-exist in the silk fibroin hydrolyzed by the protease mixture, they accelerate the effect of improving cognitive function, thereby exhibiting a rapid effect in the early stage of administration.

Analysis was performed to confirm this understanding, and as a result, it is considered that, when the peptides comprising the sequences represented by Formula 1 and 2 are contained together, the above-described acceleration effect may occur.

Therefore, according to the foregoing, it is possible to provide silk-derived peptides having the effect of improving cognitive function and memory. In particular, it is possible to produce silk-derived peptides capable of accelerating the early synergistic effect on cognitive function and memory improvement and having a further increased effect of improving memory and cognitive function.

Experimental Example 2-2: Local Ischemia-Induced Animal Model

In the same manner as described in Experimental Example 1-2 above, the following experiments were performed: A. Drug treatment and preparation of local ischemia-induced animal model; and B. Experiment on effect of peptides on decrease in area of ischemic cerebral infarction. The results are shown in FIG. 5.

Figure 5:
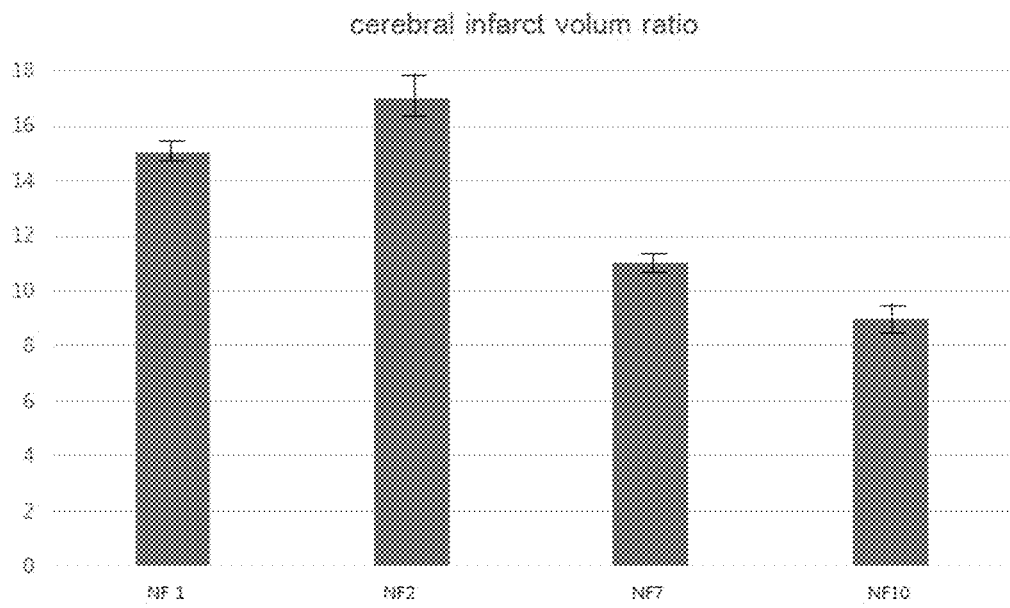

Referring to FIG. 5, it can be confirmed that the silk fibroin-derived peptides provided in the present disclosure can reduce the cerebral infarction region.

Preparation Example 3

Production of Silk-Derived Peptides

Dissolved silk fibroin was mixed with purified water, treated with 1 wt % of each of the protease compositions S1 to S11 shown in Table 9 below, and hydrolyzed for 5 hours. Thereafter, the mixtures were heat-treated for 10 minutes to remove the activities of the enzymes, and then freeze-dried to obtain the powders shown in Tables 10 below.

TABLE 9

(unit: parts by weight)

| | S1 | S2 | S3 | S4 | S5 | S6 | S7 | S8 | S9 | S10 | S11 |
|---|---|---|---|---|---|---|---|---|---|---|---|
| Flavourzyme | 100 | — | — | — | — | — | — | — | — | — | — |
| Protamex | — | 100 | — | — | — | — | — | — | — | — | — |
| Actinidin | — | — | 100 | 100 | 100 | 100 | 100 | 100 | 100 | 100 | 100 |

TABLE 9-continued (unit: parts by weight)

| | S1 | S2 | S3 | S4 | S5 | S6 | S7 | S8 | S9 | S10 | S11 |
|---|---|---|---|---|---|---|---|---|---|---|---|
| Kokulase P | — | — | — | 1 | 5 | 10 | 20 | 30 | 10 | 10 | 10 |
| Keratinase | — | — | — | 1 | 5 | 10 | 20 | 30 | 10 | 10 | 10 |
| Cathepsin K | — | — | — | — | — | — | — | — | 0.5 | 3 | 6 |

TABLE 10

| | NF1 | NF2 | TP1 | TP2 | TP3 | TP4 | TP5 | TP6 | TP7 | TP8 | TP9 |
|---|---|---|---|---|---|---|---|---|---|---|---|
| Treatment enzymes | S1 | S2 | S3 | S4 | S5 | S6 | S7 | S8 | S9 | S10 | S11 |

Experimental Example 3

Experiment on Effect of Improving Memory and Cognitive Function

Experimental Example 3-1: Animal Model Experiment for Cognitive Function Improvement According to the same methods as described in Experimental Example 1-1 above, the following experiments were performed: A. Animal model experiment on cognitive function improvement; B. Delayed alternation test; C. Administration method; and D. Results of cognitive memory assessment.

Figure 6:
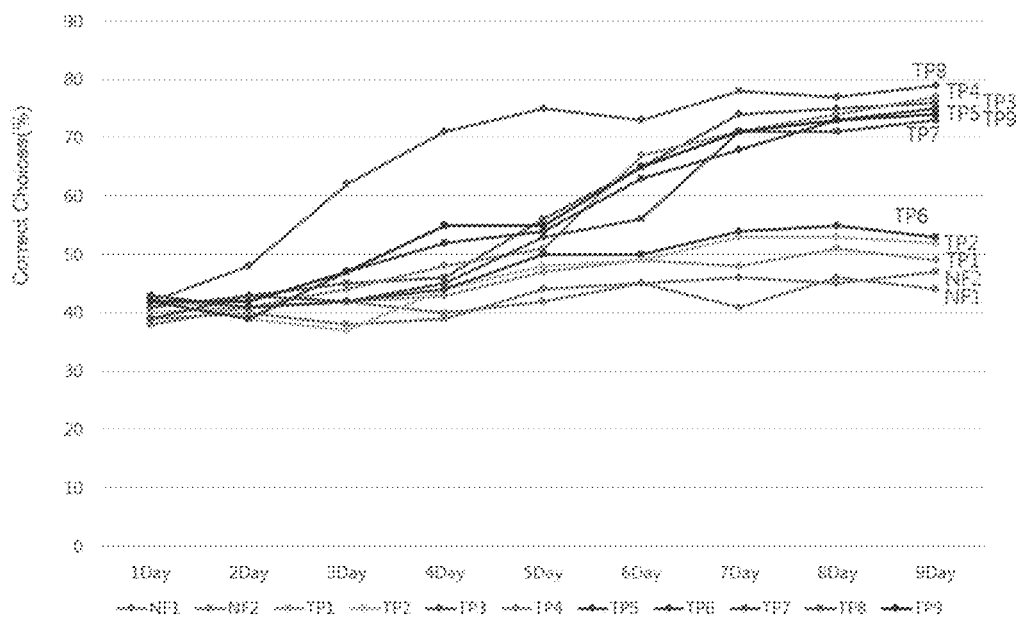

FIG. 6 shows the results of performing the T-maze test for the groups administered the silk peptides NF1, NF2 and TP1 to TP11, respectively. FIG. 6 shows the results of performing the test with a delay of 5 seconds between the trials, and indicates that the performance was gradually improved during the training period of 9 days.

The present inventors were able to obtain results with a tendency similar to that in other experiments conducted concurrently using enzyme mixtures based on papain. Referring to FIG. 6, it could be confirmed that TP5 to TP5 to TP9 clearly exhibited the effect of improving cognitive function. In addition, it could be seen that the peptides produced by the Preparation Example above also exhibited an excellent effect of improving cognitive function in the early stage.

In particular, it can be seen that TP8 exhibits an excellent effect of improving cognitive function in the early stage of administration, compared to the other peptides. Thus, it can be understood that, when certain amounts of peptides having specific sequences co-exist in the silk fibroin hydrolyzed by the protease mixture, they accelerate the effect of improving cognitive function, thereby exhibiting a rapid effect in the early stage of administration.

Experimental Example 3-2: Local Ischemia-Induced Animal Model

In the same manner as described in Experimental Example 1-2 above, the following experiments were performed: A. Drug treatment and preparation of local ischemia-induced animal model; and B. Experiment on effect of peptides on decrease in area of ischemic cerebral infarction. The results are shown in FIG. 7.

Figure 7:
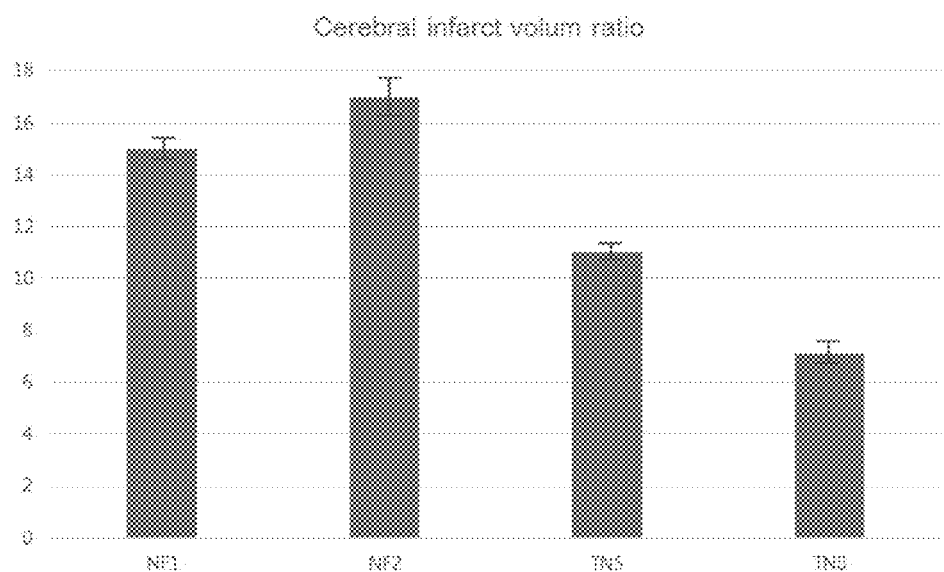

Referring to FIG. 7, it can be confirmed that the silk fibroin-derived peptides provided in the present disclosure can reduce the cerebral infarction region.

Preparation Example 4

Production of Silk-Derived Peptides

Dissolved silk fibroin was mixed with purified water, treated with 1 wt % of each of the protease compositions S1 to S11 shown in Table 11 below, and hydrolyzed for 5 hours. Thereafter, the mixtures were heat-treated for 10 minutes to remove the activities of the enzymes, and then freeze-dried to obtain the powders shown in Tables 12 below.

TABLE 11

(unit: parts by weight)

| | S1 | S2 | S3 | S4 | S5 | S6 | S7 | S8 | S9 | S10 | S11 |
|---|---|---|---|---|---|---|---|---|---|---|---|
| Flavourzyme | 100 | — | — | — | — | — | — | — | — | — | — |
| Protamex | — | 100 | — | — | — | — | — | — | — | — | — |
| Ficin | — | — | 100 | 100 | 100 | 100 | 100 | 100 | 100 | 100 | 100 |
| Kokulase P | — | — | — | 1 | 5 | 10 | 20 | 30 | 10 | 10 | 10 |
| Keratinase | — | — | — | 1 | 5 | 10 | 20 | 30 | 10 | 10 | 10 |
| Cathepsin K | — | — | — | — | — | — | — | — | 0.5 | 3 | 6 |

TABLE 12

|  | NF1 | NF2 | TN1 | TN2 | TN3 | TN4 | TN 5 | TN6 | TN7 | TN8 | TN9 |
|---|---|---|---|---|---|---|---|---|---|---|---|
| Treatment enzymes | S1 | S2 | S3 | S4 | S5 | S6 | S7 | S8 | S9 | S10 | S11 |

Experimental Example 4

Experiment on Effect of Improving Memory and Cognitive Function

Experimental Example 4-1: Animal Model Experiment for Cognitive Function Improvement According to the same methods as described in Experimental Example 1-1 above, the following experiments were performed: A. Animal model experiment on cognitive function improvement; B. Delayed alternation test; C. Administration method; and D. Results of cognitive memory assessment.

Figure 9:
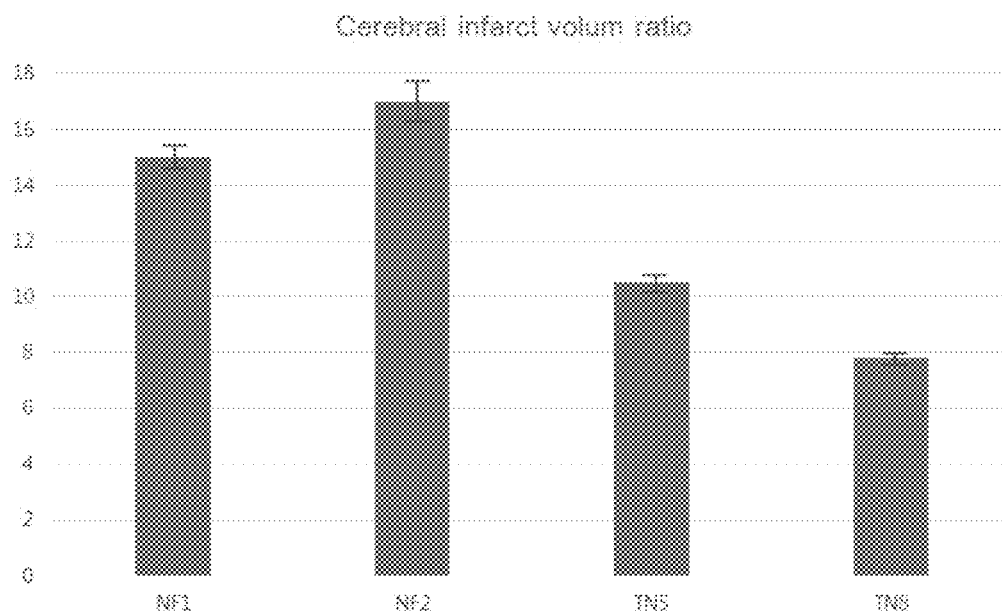

FIG. 9 shows the results of performing the T-maze test for the groups administered the silk peptides NF1, NF2 and TN1 to TN9, respectively. FIG. 9 shows the results of performing the test with a delay of 5 seconds between the trials, and indicates that the performance was gradually improved during the training period of 9 days.

Figure 8:
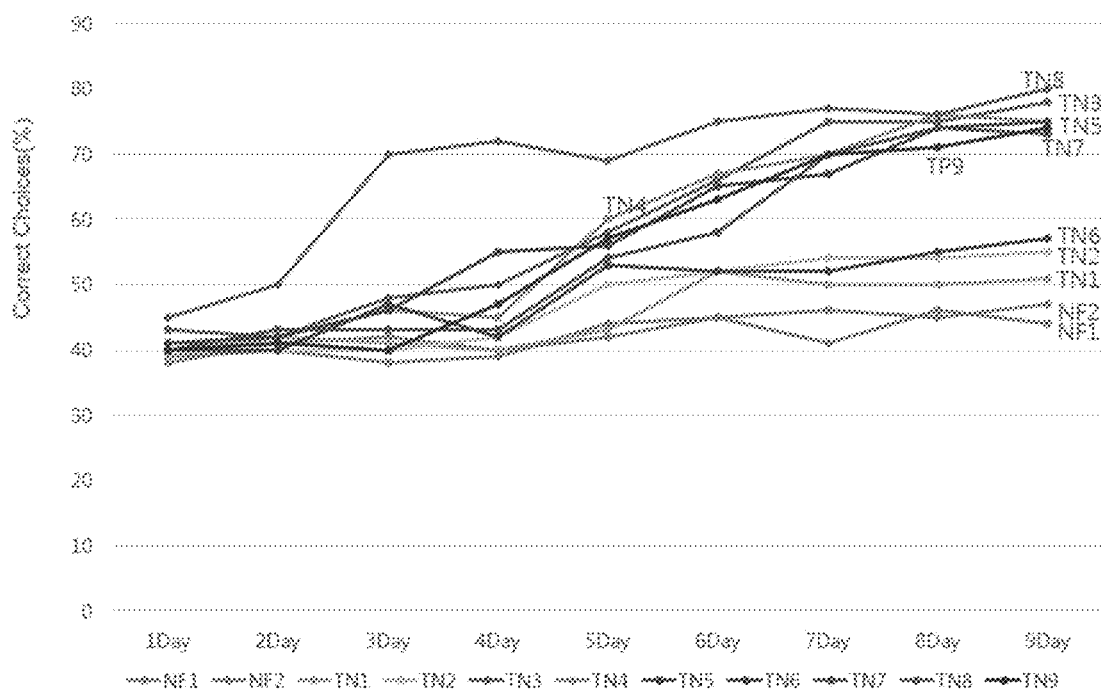

The present inventors were able to obtain results with a tendency similar to that in other experiments conducted concurrently using enzyme mixtures based on papain. Referring to FIG. 8, it could be confirmed that TN3 to TN5 and TN7 to TN9 clearly exhibited the effect of improving cognitive function. In addition, it could be seen that the peptides produced by the Preparation Example above also exhibited an excellent effect of improving cognitive function in the early stage.

In particular, it can be seen that TN8 exhibits an excellent effect of improving cognitive function in the early stage of administration, compared to the other peptides. Thus, it can be understood that, when certain amounts of peptides having specific sequences co-exist in the silk fibroin hydrolyzed by the protease mixture, they accelerate the effect of improving cognitive function, thereby exhibiting a rapid effect in the early stage of administration.

Analysis was performed to confirm this understanding, and as a result, it is considered that, when a peptide comprising the amino acid sequence represented by Formula 1a or 1b, and a peptide comprising the amino acid sequence represented by Formula 1 are contained together, the above-described acceleration effect may occur.

Experimental Example 4-2: Local Ischemia-Induced Animal Model

In the same manner as described in Experimental Example 1-2 above, the following experiments were performed: A. Drug treatment and preparation of local ischemia-induced animal model; and B. Experiment on effect of peptides on decrease in area of ischemic cerebral infarction. The results are shown in FIG. 9.

Referring to FIG. 9, it can be confirmed that the silk fibroin-derived peptides provided in the present disclosure can reduce the cerebral infarction region.

Preparation Example 5

Production of Silk Fibroin Powders

Silk fibroin (R1) from which sericin has been removed was treated as shown in Table 13 below, thereby preparing silk fibroin powders R2 to R4.

TABLE 13

| R1 | Silk fibroin from which sericin has been removed. |
|---|---|
| R2 | Powder was prepared by mixing silk fibroin with alcohol, followed by grinding and drying. |
| R3 | Powder was prepared by mixing silk fibroin with glycerol, followed by grinding, washing with water, and drying. |
| R4 | Powder was prepared from atmospheric pressure plasma-treated silk fibroin in the same manner as P3. |

Experimental Example 5

Preparation of Silk Fibroin Powder

For the fibroin powders R2 to R4 produced as shown in Table 13 above, the amount of calcium chloride solution required to completely dissolve the silk fibroin powder so as to be able to be hydrolyzed was evaluated while the calcium chloride solution was added to each of the silk fibroin solutions R1 to R4 at a maintained temperature of 50° C. The amount of the calcium chloride solution was expressed as a percentage relative to the weight of the silk fibroin powder used as a solute.

TABLE 14

|  | R1 | R2 | R3 |
|---|---|---|---|
| Calcium chloride solution | 830% | 130% | 80% |

Referring to Table 14 above, it can be seen that, according to R2 and R3, even when a relatively very small amount of the calcium chloride solution is used, it can completely dissolve the silk fibroin. In particular, it can be confirmed that the silk protein can have excellent solubility even at a temperature lower than that in the prior art.

Thus, when the silk fibroin powder is used, the amount of calcium chloride solution used as a solvent can be significantly reduced, and thus the process efficiency can be increased by miniaturizing a reactor that is used in the step of dissolving silk fibroin and the step of hydrolyzing. In addition, it can be seen that since the amount of calcium chloride used can be reduced, it is possible to reduce the amount and time of water required to remove the salt, thereby achieving process efficiency.

The same results could be obtained by performing the same experiments as in Experimental Examples 1 to 3 using the produced silk fibroin powder. Therefore, it can be confirmed that the use of the silk fibroin powder makes it possible to increase the efficiency of the dissolution and hydrolysis processes.

Analysis of Sequences of Silk Hydrolysates

In order to find peptides exhibiting the above-described synergistic effect, the peptides contained in the silk fibroin hydrolyzate were analyzed. In addition, peptides that cause the acceleration effect and synergistic effect were selected as compared with the conventionally known peptides. As a result of the analysis, it was confirmed that, when the peptides represented by Formulas 1 to 5 below were included, the synergistic effect in the early stage and the acceleration effect occurred.

In particular, in order to confirm the synergistic effect and acceleration effect of the peptides represented by Formulas 1 to 5, the peptides consisting of the amino acid sequences of Formulas 1 to 5, respectively, were synthesized, and an experiment on the effects of the synthesized peptides on the improvement of cognitive function was performed.

Tyr-Gly-$X_1$—$X_2$     [Formula 1]

wherein $X_1$ is Ala, Tyr, Thr, Val, Gly, Ile or Gln, and $X_2$ is Ala, Tyr, Ile, Val or Gly.

Ile-Gly-$Z_1$—$Z_2$     [Formula 2]

wherein $Z_1$ is Ala, Tyr, Val or Gln, and $Z_2$ is Ala, Tyr, Val or Gly.

Ile-Gly-Val-$a_1$-$a_2$     [Formula 3]

wherein $a_1$ is Ala, Tyr or Val, and $a_2$ is Ala, Tyr, Thr, Val, Gly or Gln.

$a_1$-Gly-Gly-$a_1$     [Formula 4]

wherein $a_1$ is Ala, Tyr or Val.

$a_1$-Gly-Gly-$a_1$-Gly-$a_2$     [Formula 5]

wherein $a_1$ is Ala, Tyr or Val, and $a_2$ is Ala, Tyr, Ile or Val.

Preparation Example 6

Synthesis and Mixing of Peptides

In order to examine whether the peptides predicted as described exhibit the effect of improving cognitive function and memory within a short period of time, the peptides P1-1 to P1-6 were synthesized by an outside manufacturer.

In addition, in order to confirm whether each mixtures of peptide exhibits a synergistic effect, the peptides P2-1 to P2-4 shown in Table 2 above were synthesized, and the synthesized peptides were mixed together according to the compositions shown in Table 15 below, thereby preparing peptide compositions.

TABLE 15

(unit: parts by weight)

| | P1-6 | M1 | M2 | M3 | M4 |
|---|---|---|---|---|---|
| P1-6 | 100 | 100 | 100 | 100 | 100 |
| P2-1 | — | 50 | — | — | — |
| P2-2 | — | — | 50 | — | — |
| P2-3 | — | — | — | 50 | — |
| P2-4 | — | — | — | — | 50 |

Experimental Example 6

Experiment on Effect of Improving Memory and Cognitive Function

Experimental Example 6-1: Animal Model Experiment for Cognitive Function Improvement According to the same methods as described in Experimental Example 1-1 above, the following experiments were performed: A. Animal model experiment on cognitive function improvement; B. Delayed alternation test; C. Administration method; and D. Results of cognitive memory assessment.

Figure 10:
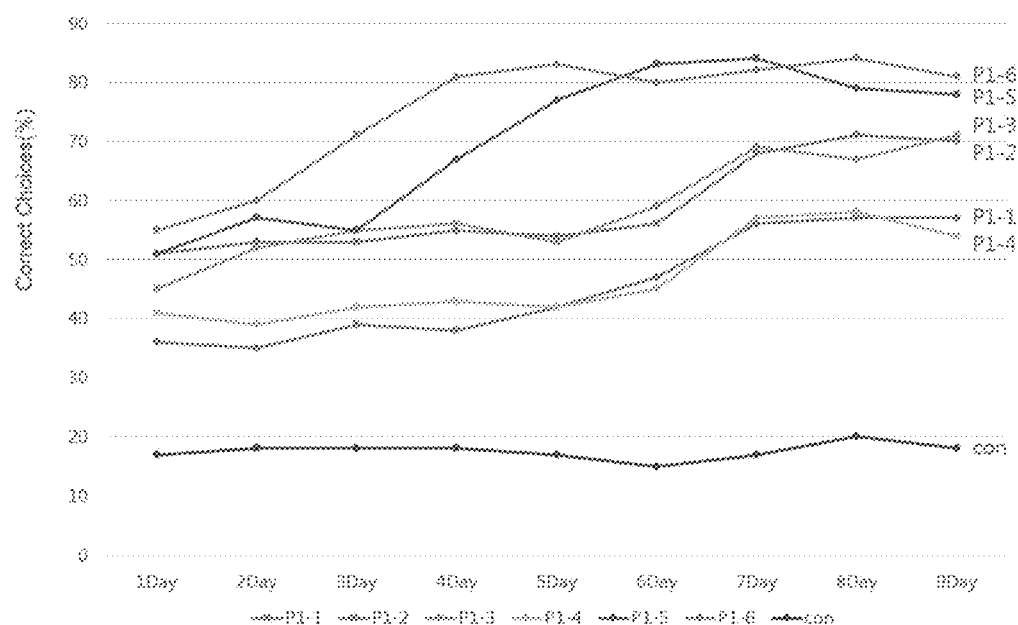
FIGS. 10, 11, 12, 13, 14 and 15 show the results of evaluating the effects of peptides according to the examples of the present disclosure on the improvement of cognitive function and memory.
Figure 11:
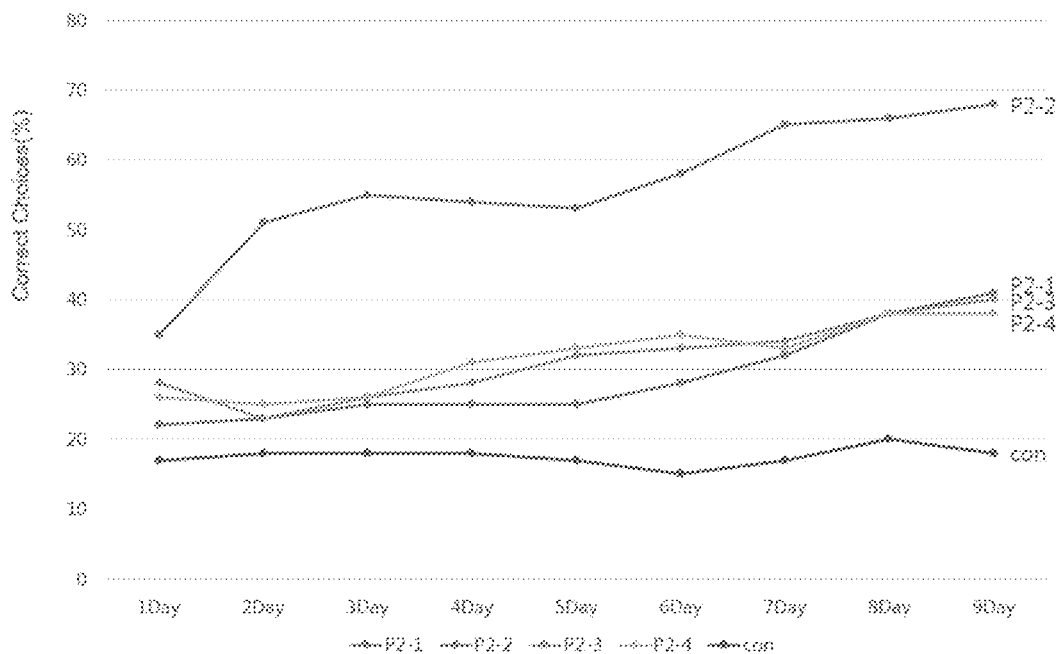

FIGS. 10 and 11 show the results of performing the T-maze test for the groups administered P1-1 to P1-6 and M1 to M4, respectively. FIGS. 10 and 11 show the results of performing the test with a delay of 5 seconds between the trials, and indicate that the performance was gradually improved during the training period of 9 days.

Referring to FIG. 10, it can be seen that the peptides P1-1 to P1-6 disclosed in the present disclosure generally improve cognitive memory. In addition, it can be seen that the peptides P1-2, P1-3, P1-5 and P1-6 have an increased effect of improving cognitive function and memory, compared to the peptides P1-1 and P1-4.

Meanwhile, it could be confirmed that the peptide P1-6 had a significantly increased effect of improving cognitive function and memory in the early stage of administration, compared to the other synthesized peptides.

Figure 12:
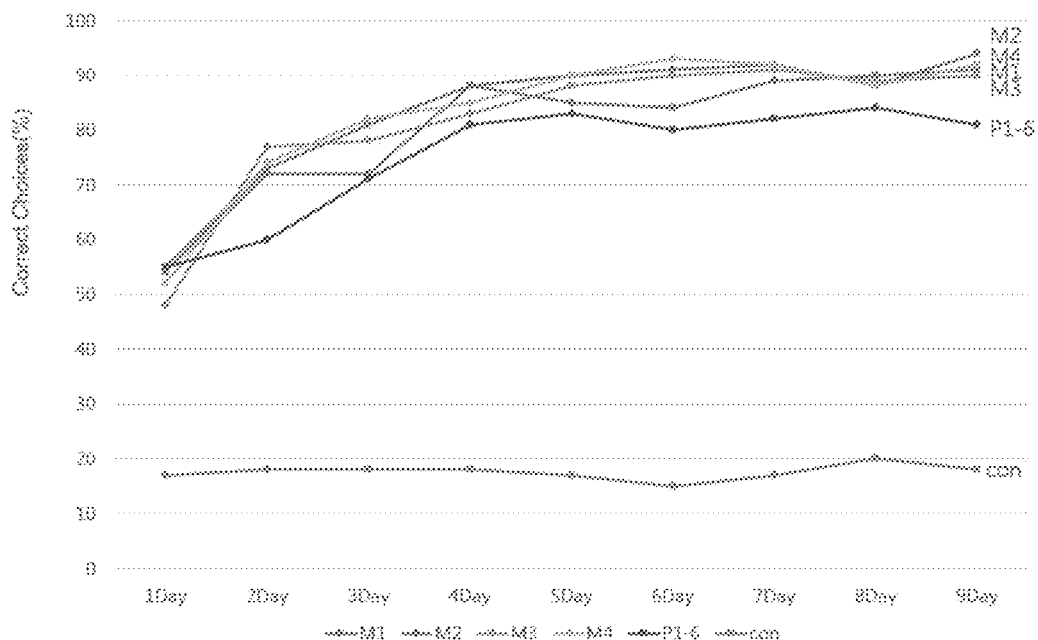

Referring to FIG. 12, it can be seen that, when P2-1 to P2-4 are mixed together, like M1 to M4 disclosed in the present disclosure, they have not only a synergistic effect of improving cognitive function and memory, but also a significantly increased effect of improving cognitive function and memory in the early stage. That is, referring to FIG. 11, the effect of P2-2 on the improvement of cognitive function and memory is relatively better, but the effects of P2-1, P2-3 and P2-4 themselves on the improvement of cognitive function and memory are relatively low. However, it can be seen that, when a peptide composition is provided by mixing any one or more of P2-1 to P2-4 with the peptide of Formula 1, it has a synergistic effect due to interaction between the peptides, thus exhibiting a significantly increased effect of improving cognitive function and memory and a significantly increased effect of improving cognitive function and memory in an early stage. Therefore, it can be confirmed that, when a peptide composition is formed by mixing the peptide of Formula 1 and the peptide of Formula 2, it can provide a composition exhibiting an excellent effect of improving cognitive function and memory and fast early-stage activity.

In particular, the early-stage activity of a food or a medicament for improving cognitive function and memory is considerably important. Thus, the present disclosure may provide a food or medicament having an increased effect of improving cognitive function and memory and an increased effect of improving cognitive function and memory in an early stage.

Preparation Example 7

Synthesis and Mixing of Peptides

Based on the above-described experimental results, the peptides F1, F2 and F3 shown in Table 3 were synthesized by an outside manufacturer.

Experimental Example 7

Experiment on Effect of Improving Memory and Cognitive Function

Experimental Example 7-1: Animal Model Experiment for Cognitive Function Improvement An experiment was performed in the same manner as Experimental Example 6 to confirm whether the synthesized peptides F1, F2 and F3 improve cognitive function.

Figure 13:
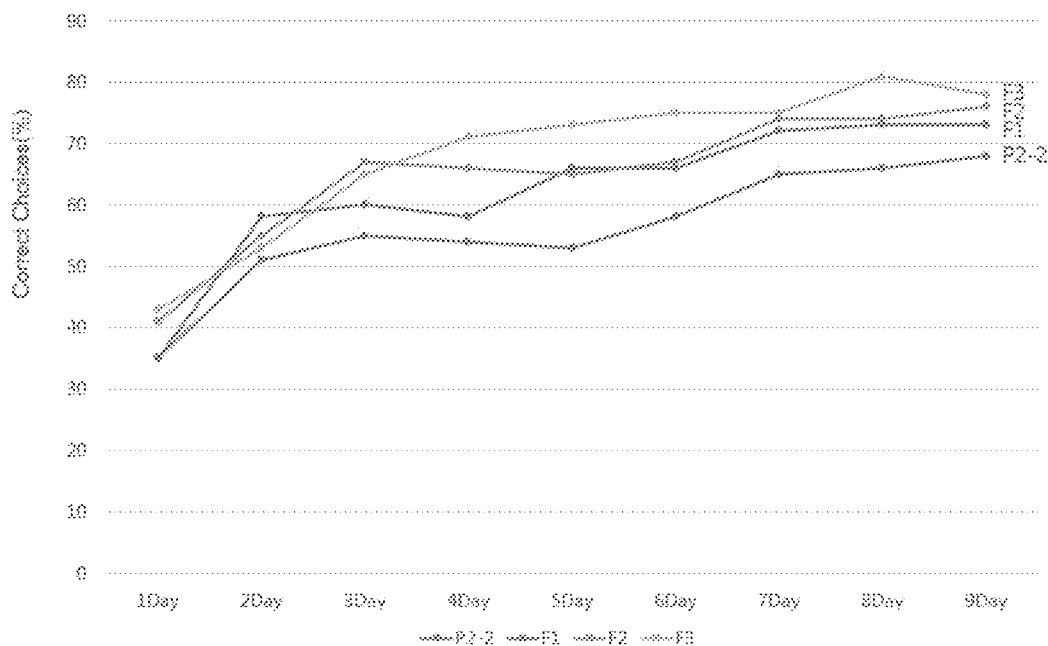

Referring to FIG. 13, it could be confirmed that F1, F2 and F3 generally exhibited a high effect of improving cognitive function and memory, compared to P2-2. In addition, it could be confirmed that F1, F2, F3 also had a high activity of improving cognitive function and memory in an early stage, compared to P2-2.

Preparation Example 8

Synthesis and Mixing of Peptides

Among the silk fibroin hydrolysates, hydrolysates exhibiting the effect of improving cognitive function and memory within a short period of time were analyzed, and peptides capable of exhibiting a rapid effect were predicted.

In order to examine whether the peptides predicted as described exhibit the effect of improving cognitive function and memory within a short period of time, the peptides P4-1 to P4-3 and P5-1 to P5-4 were synthesized by an outside manufacturer.

In addition, in order to confirm whether each mixture of peptides exhibits a synergistic effect, the peptides P2-1 to P2-4 shown in Table 2 above were synthesized, and the synthesized peptides were mixed together according to the compositions shown in Table 16 below, thereby preparing peptide compositions.

TABLE 16

(unit: parts by weight)

| | P5-1 | M1 | M2 | M3 | M4 |
|---|---|---|---|---|---|
| P5-1 | 100 | 100 | 100 | 100 | 100 |
| P2-1 | — | 50 | — | — | — |
| P2-2 | — | — | 50 | — | — |
| P2-3 | — | — | — | 50 | — |
| P2-4 | — | — | — | — | 50 |

Experimental Example 8

Experiment on Effect of Improving Memory and Cognitive Function

Experimental Example 8-1: Animal Model Experiment for Cognitive Function Improvement According to the same methods as described in Experimental Example 1-1 above, the following experiments were performed: A. Animal model experiment on cognitive function improvement; B. Delayed alternation test; C. Administration method; and D. Results of cognitive memory assessment.

Figure 14:
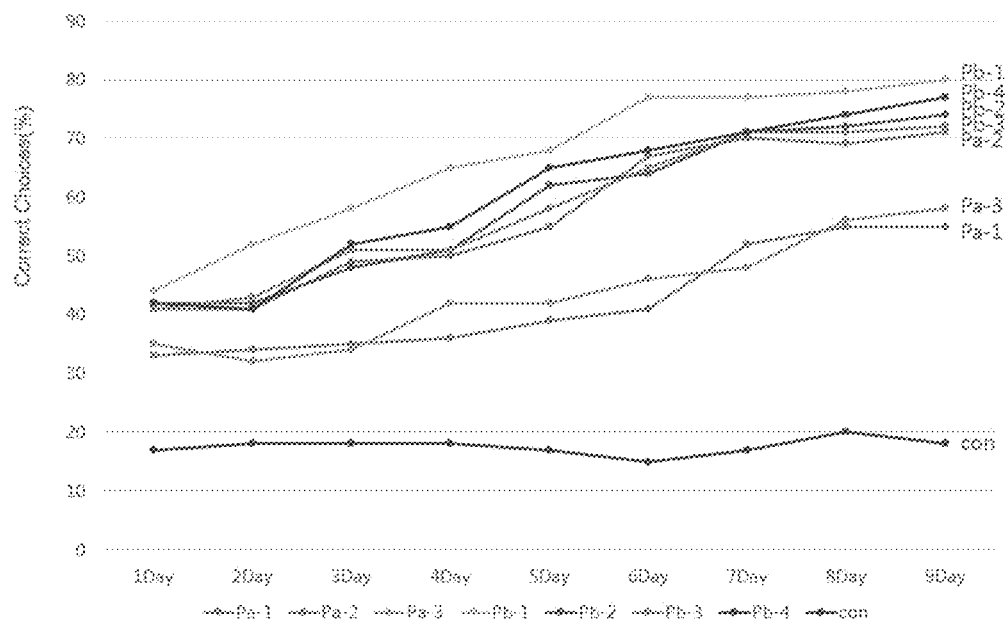
Figure 15:
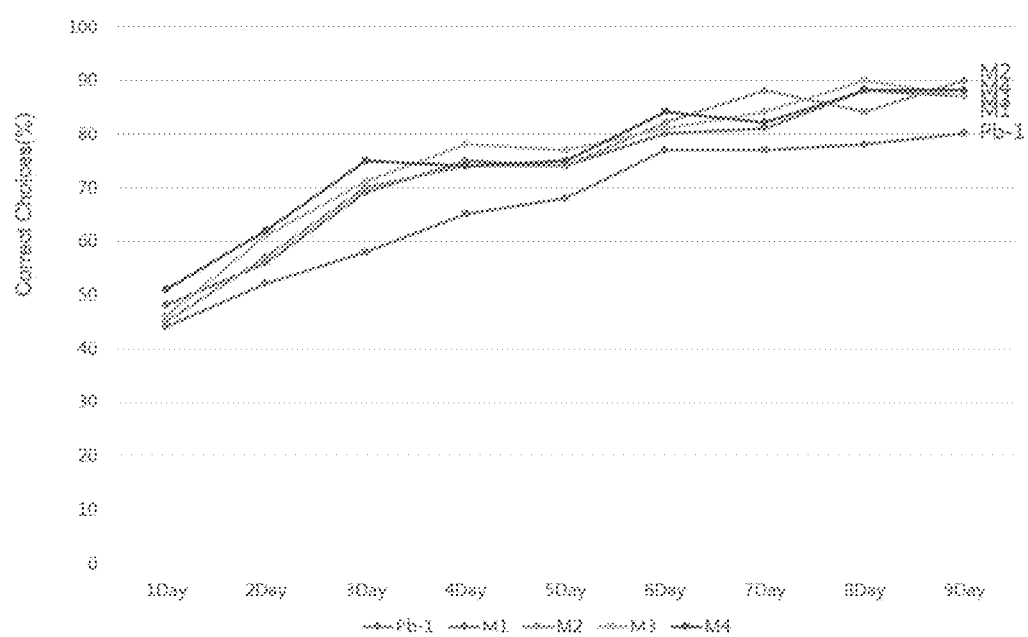

FIGS. 14 and 15 show the results of performing the T-maze test for the groups administered P1-1 to P1-6 and M1 to M4, respectively. FIGS. 14 and 15 show the results of performing the test with a delay of 5 seconds between the trials, and indicate that the performance was gradually improved during the training period of 9 days.

Referring to FIG. 14, it can be seen that the peptides P4-1 to P4-3 disclosed in the present disclosure generally improve cognitive memory. In addition, it can be seen that the peptide P4-2 have an increased effect of improving cognitive function and memory, compared to the other peptides P4-1 and P1-3. In particular, it could be confirmed that the peptide P4-1 had a significantly increased effect of improving cognitive function and memory in the early stage of administration, compared to the other synthesized peptides.

In addition, it could be confirmed that P5-1 to P5-4 exhibited an excellent effect of improving cognitive function and memory, compared to P4-1 and P4-3. In particular, it could be confirmed that P5-1 not only exhibited a clearly better effect of improving cognitive function and memory than P4-2, but also had an excellent activity of improving cognitive function and memory in the early stage.

Referring to FIG. 15, it can be seen that, when M1 to M4 disclosed in the present disclosure are additionally mixed and used, they have not only a synergistic effect due to interaction between the peptides, but also a significantly increased effect of improving cognitive function and memory in the early stage. That is, referring to FIG. 11, the effect of P2-2 on the improvement of cognitive function and memory is relatively better, but the effects of P2-1, P2-3 and P2-4 themselves on the improvement of cognitive function and memory are relatively low. However, it can be seen that, when a peptide composition is provided by mixing any one or more of P2-1 to P2-4 with the peptide represented by Formula 4 or 5, it has a synergistic effect due to interaction between the peptides, thus exhibiting a significantly increased effect of improving cognitive function and memory and a significantly increased effect of improving cognitive function and memory in an early stage.

Therefore, it can be confirmed that, when a peptide composition is formed by mixing the peptide of Formula 4 or 5 and the peptide of Formula 2, it can provide a composition exhibiting an excellent effect of improving cognitive function and memory and fast early-stage activity.

Therefore, it can be seen that peptides produced according to the method for producing a peptide for improving memory and preventing or alleviating cognitive dysfunction according to the present disclosure can exhibit an acceleration effect and a synergistic effect. In addition, when the above-specified peptides are produced by a method available by those skilled in the art and are included in a product, these peptides can exhibit an excellent synergistic effect on cognitive function improvement and the like together with a significantly increased effect of improving cognitive function in an early stage, compared to a conventional art.

As described above, the present disclosure provides a peptide having an excellent effect of improving cognitive function, particularly an excellent effect of improving cognitive function in an early stage, a composition comprising the same, and a method for producing the same.

The present disclosure provides a method for producing a silk-derived peptide, which is capable of more effectively producing the silk-derived peptide using a protease.

According to the present disclosure, it is possible to miniaturize an existing process system while maintaining the same production of a final product, and it is possible to produce a silk-derived peptide with a high yield within a short time by a small process.

Although the preferred embodiments of the present disclosure have been described above in detail, the scope of the present disclosure is not limited thereto. Those skilled in the art will appreciate that various modifications and improvements are possible, without departing from the basic concept of the present disclosure as defined in the appended claims, and also fall within the scope of the present disclosure.

What is claimed is:

1. A peptide selected from the group consisting of the amino acid sequence represented by the following Formula 1:

Tyr-Gly-$X_1$—$X_2$     [Formula 1], wherein $X_1$ is Tyr or Gln, and $X_2$ is Ala or Val.

2. A peptide composition for improving memory and preventing or alleviating cognitive dysfunction comprising the peptide of claim 1.

3. The peptide composition of claim 2, which is derived from silk fibroin.

\* \* \* \* \*